United States Patent [19]

Ife et al.

[11] Patent Number: 5,064,833

[45] Date of Patent: Nov. 12, 1991

[54] SUBSTITUTED QUINAZOLINE DERIVATIVES FOR USE IN GASTROINTESTINAL DISEASES

[75] Inventors: Robert J. Ife, Stevenage; Thomas H. Brown, Tewin; Colin A. Leach, Stevenage; David J. Keeling, Harpenden, all of England

[73] Assignee: Smithkline Beecham Intercredit B.V., Welwyn Garden City, United Kingdom

[21] Appl. No.: 520,561

[22] Filed: May 8, 1990

Related U.S. Application Data

[63] Continuation-in-part of Ser. No. 467,075, Jan. 18, 1990, abandoned, which is a continuation-in-part of Ser. No. 278,064, Nov. 30, 1988, abandoned.

[30] Foreign Application Priority Data

May 10, 1989 [GB] United Kingdom ............ 8910722

[51] Int. Cl.$^5$ ............ A61K 31/505; C07D 239/95
[52] U.S. Cl. ............ 514/260; 514/31.5; 514/232.5; 544/80; 544/119; 544/283; 544/285; 544/286; 544/287; 544/291; 544/292; 544/293
[58] Field of Search ............ 544/291, 293, 80, 119; 514/260, 231.5, 232.5

[56] References Cited

U.S. PATENT DOCUMENTS

| | | | |
|---|---|---|---|
| 2,945,859 | 7/1960 | Hitchings et al. | 544/291 |
| 3,511,836 | 5/1970 | Hess | 544/291 |
| 3,560,502 | 2/1971 | Davoll | 544/291 |
| 3,635,979 | 1/1972 | Hess et al. | 544/291 |
| 3,669,968 | 6/1972 | Hess | 544/291 |
| 3,920,636 | 11/1975 | Takahashi | 544/291 |
| 3,956,495 | 5/1976 | Lacefield | 544/291 |
| 4,001,237 | 1/1977 | Partyka et al. | 544/291 |
| 4,001,238 | 1/1977 | Partyka et al. | 544/291 |
| 4,098,788 | 7/1978 | Crenshaw et al. | 544/293 |
| 4,287,341 | 9/1981 | Hess et al. | 544/291 |
| 4,502,880 | 3/1985 | Holyoke | 544/284 |
| 4,677,219 | 6/1987 | Berman et al. | 544/291 |
| 4,818,753 | 4/1989 | Colwell et al. | 544/291 |

FOREIGN PATENT DOCUMENTS

| | | | |
|---|---|---|---|
| 579572 | 7/1959 | Canada | 544/291 |
| 28473 | 3/1985 | European Pat. Off. | |
| 1310457 | 7/1988 | France. | |
| 457460 | 9/1989 | Switzerland. | |
| 806772 | 12/1958 | United Kingdom. | |
| 1390014 | 4/1975 | United Kingdom. | |

OTHER PUBLICATIONS

E. F. Elslager et al., J. Med. Chem. 1981, 24, 127–140.

Primary Examiner—C. Warren Ivy
Assistant Examiner—James H. Turnipseed
Attorney, Agent, or Firm—Linda E. Hall; Stuart R. Suter; Edward T. Lentz

[57] ABSTRACT 2,4-diaminoquinazoline compounds are inhibitors of the H+K+ATPase enzyme and useful for the treatment of diseases of the stomach based on excessive gastric acid secretion. A compound of the invention is 2-[2-methyl-4-fluorophenyl)amino]-4-(N-methylphenylamino)-quinazoline.

40 Claims, No Drawings

SUBSTITUTED QUINAZOLINE DERIVATIVES FOR USE IN GASTROINTESTINAL DISEASES

This application is a continuation-in-part of co-pending application Ser. No. 467,075, filed Jan. 18, 1990, now abandoned, which is a continuation-in-part of copendending application Ser. No. 278,064, filed Nov. 30, 1988, now abandoned.

The present invention relates to substituted quinazoline derivatives, processes for their preparation, intermediates useful in their preparation, pharmaceutical compositions containing them and their use in therapy.

Accordingly the present invention provides, in a first aspect compounds of structure (I)

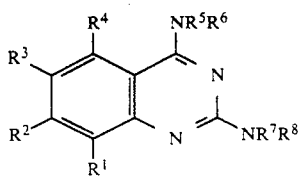

in which
R$^1$ to R$^4$ are the same or different and are each hydrogen, C$_{1-4}$alkyl, C$_{1-4}$alkoxy, phenyl, C$_{1-4}$alkylthio, C$_{1-4}$alkanoyl, amino, C$_{1-6}$alkylamino, diC$_{1-4}$alkylamino, halogen, trifluoromethyl, hydroxy, hydroxyC$_{1-4}$alkyl, hydroxyC$_{1-4}$alkoxy, carboxyC$_{1-4}$alkoxy, C$_{1-4}$alkoxy-C$_{1-4}$alkoxy, O(CH$_2$)$_m$Het, C$_{1-4}$alkylNR$^9$R$^{10}$ or O(CH$_2$)$_m$NR$^9$R$^{10}$ in which m is 2 to 4 and R$^9$ and R$^{10}$ are the same or different and are each hydrogen, C$_{1-4}$alkyl, Het or —(CH$_2$)$_n$Ar where n is 0 to 4, Ar is an optionally substituted phenyl ring, m is 2 to 4 and Het is an optionally substituted heterocyclic ring, or R$^9$ and R$^{10}$ together with the nitrogen to which they are attached form a saturated or unsaturated ring optionally containing one or more further heteroatoms; provided that at least two of R$^1$ to R$^4$ are hydrogen.

R$^5$ and R$^6$ are the same, or different and are each hydrogen, C$_{1-4}$alkyl, —(CH$_2$)$_n$Ar in which n is 0 to 4 and Ar is an optionally substituted phenyl group, or R$^5$ and R$^6$ together with the nitrogen atom to which they are attached form a saturated or unsaturated ring optionally containing one or more further heteroatoms; and R$^7$ and R$^8$ are the same or different and are each hydrogen, C$_{1-4}$alkyl, (CH$_2$)$_n$Ar$^1$ in which n is 0 to 4 and Ar$^1$ is an optionally substituted phenyl group, or R$^7$ and R$^8$ together with the nitrogen atom to which they are attached form a saturated or unsaturated ring optionally containing one or more further heteroatoms;

and pharmaceutically acceptable salts thereof, provided that when R$^1$ to R$^4$ are the same or different and are each hydrogen, C$_{1-4}$alkyl, C$_{1-4}$alkoxy, phenyl, C$_{1-4}$alkylthio, C$_{1-4}$alkanoyl, amino, C$_{1-4}$alkylamino, diC$_{1-4}$alkylamino, halogen or trifluoromethyl, then (a) R$^5$, R$^6$, R$^7$ and R$^8$ are not all hydrogen;
(b) at least one of R$^5$ or R$^6$ is (CH$_2$)$_n$Ar; or R$^7$ or R$^8$ is (CH$_2$)$_n$Ar$^1$;
(c) when R$^1$ and R$^4$ are hydrogen, and either one of R$^2$ or R$^3$ is C$_{1-4}$alkoxy, the other is not hydrogen or C$_{1-4}$alkoxy.

Suitably at least two of R$^1$ to R$^4$ are hydrogen and the others are the same or different and are each hydrogen, C$_{1-4}$alkyl, C$_{1-4}$alkoxy, phenyl, C$_{1-4}$alkylthio, C$_{1-4}$alkanoyl, C$_{1-4}$alkylamino, diC$_{1-4}$alkylamino, halogen, trifluoromethyl or nitro. More suitably, three of R$^1$ to R$^4$ are hydrogen and the other is hydrogen, C$_{1-4}$alkyl, C$_{1-4}$alkoxy, phenyl, C$_{1-4}$alkylthio, C$_{1-4}$alkanoyl, amino, C$_{1-4}$alkylamino, diC$_{1-4}$alkylamino, halogen, trifluoromethyl, hydroxy, hydroxyC$_{1-4}$alkyl, carboxyC$_{1-4}$alkoxy, hydroxyC$_{1-4}$alkoxy, C$_{1-4}$alkoxyC$_{1-4}$alkoxy, O(CH$_2$)$_m$Het, C$_{1-4}$alkylNR$^9$R$^{10}$ or O(CH$_2$)$_m$NR$^9$R$^{10}$; preferably R$^2$ to R$^4$ are hydrogen and R$^1$ is hydrogen, C$_{1-4}$alkoxy, hydroxy, or O(CH$_2$)$_m$NR$^9$R$^{10}$; hydroxy or O(CH$_2$)$_m$NR$^9$R$^{10}$, or R$^1$R$^2$ and R$^4$ are hydrogen and R$^3$ is hydroxy or O(CH$_2$)$_m$NR$^9$R$^{10}$.

Suitably R$^5$ and R$^6$ are the same or different and are each hydrogen or (CH$_2$)$_n$Ar in which n is 0 to 4 and Ar is an optionally substituted phenyl group or R$^5$ and R$^6$ together with the nitrogen atom to which they are attached form a saturated or unsaturated carbocyclic ring. More suitably, one of R$^5$ and R$^6$ is hydrogen or C$_{1-4}$alkyl and the other is hydrogen, C$_{1-4}$alkyl or (CH$_2$)$_n$Ar. Most suitably one of R$^5$ and R$^6$ is hydrogen or C$_{1-4}$alkyl and the other is (CH$_2$)$_n$Ar. Preferably one of R$^5$ and R$^6$ is C$_{1-4}$alkyl and the other is (CH$_2$)$_n$Ar; most preferably one of R$^5$ and R$^6$ is C$_{1-4}$alkyl, in particular methyl and the other is (CH$_2$)$_n$Ar in which n is 0.

Suitably, Ar is unsubstituted or substituted by 1 to 3 substituents selected from hydrogen, C$_{1-4}$alkyl, C$_{1-4}$alkoxy, C$_{1-4}$alkylthio, halogen, cyano, amino, hydroxy, carbamoyl, carboxy, C$_{1-4}$alkanoyl or trifluoromethyl. More suitably, Ar is unsubstituted or substituted by two substituents selected from hydrogen, C$_{1-4}$alkyl, C$_{1-4}$alkoxy, C$_{1-4}$alkylthio, halogen, cyano, amino, hydroxy, carbamoyl, carboxy, C$_{1-4}$alkanoyl or trifluoromethyl. More preferably, Ar is unsubstituted or substituted by two substituents selected from C$_{1-4}$alkyl and C$_{1-4}$alkoxy. Most preferably, Ar is unsubstituted or substituted by a single substituent selected from the above-noted groups, in particular, hydroxy, halogen, C$_{1-4}$alkyl or C$_{1-4}$alkoxy.

Suitably, R$^7$ and R$^8$ are the same or different and are each hydrogen, C$_{1-4}$alkyl, (CH$_2$)$_n$Ar$^1$ in which n is 0 to 4 and Ar$^1$ is an optionally substituted phenyl group, or R$^7$ and R$^8$ together with the nitrogen atom to which they are attached form a saturated or unsaturated carbocyclic ring. More suitably one of R$^7$ and R$^8$ is hydrogen or C$_{1-4}$alkyl and the other is hydrogen, C$_{1-4}$alkyl or (CH$_2$)$_n$Ar$^1$, or R$^7$ and R$^8$ together with the nitrogen atom to which they are attached form a saturated or unsaturated ring. Most suitably, one of R$^7$ and R$^8$ is hydrogen or C$_{1-4}$alkyl and the other is hydrogen, C$_{1-4}$alkyl or (CH$_2$)$_n$Ar$^1$. Preferably one of R$^7$ and R$^8$ is hydrogen or C$_{1-4}$alkyl and the other is (CH$_2$)$_n$Ar$^1$; more preferably one of R$^7$ and R$^8$ is hydrogen and the other is (CH$_2$)$_n$Ar$^1$; most preferably, one of R$^7$ and R$^8$ is hydrogen and the other is (CH$_2$)$_n$Ar$^1$ in which n is 0.

Suitably, the group Ar$^1$ is unsubstituted or optionally substituted by 1 to 3 substituents as hereinabove described for the group Ar in R$^5$. Preferably the group Ar$^1$ is unsubstituted or optionally substituted by two substituents as hereinabove described for Ar. Preferably the group Ar$^1$ is unsubstituted or substituted by two groups, which may be the same or different; more preferably the group Ar$^1$ is unsubstituted or substituted by two groups which may be the same or different and selected from C$_{1-4}$alkyl and C$_{1-4}$alkoxy. Most preferably the group Ar$^1$ is unsubstituted or substituted by one or two groups, for example a C$_{1-4}$alkyl group, in particular a methyl group or a halogen atom, in particular a fluorine atom; or a $C_{1-4}$alkyl group and a halogen atom in particular a methyl group and fluorine atom. Particularly preferably the group $Ar^1$ is substituted by a methyl group in the 2-position of the ring and a fluorine atom in the 4-position of the ring.

Suitably $R^9$ and $R^{10}$ are the same or different and are each hydrogen, $C_{1-4}$alkyl, Het, or $(CH_2)_nAr$, or $R^9$ and $R^{10}$ together with the nitrogen atom to which they are attached form a saturated or unsaturated ring optionally containing one or more further heteroatoms. Suitable and preferred groups Ar are as hereinbefore defined for $R^5$ and $R^6$ More suitably, $R^9$ and $R^{10}$ are the same and are each $C_{1-4}$alkyl.

Het groups (either alone or as part of another group) include, for example, 5- or 6- membered heterocyclic rings containing one or more heteroatoms, such as pyridyl and imidazolyl groups.

Suitable saturated or unsaturated rings optionally containing one or more heteroatoms include for example, piperidino, morpholino, imidazolyl and pyridyl rings.

Suitably m is 2 to 4, preferably m is 3.

$C_{1-4}$alkyl groups (either alone or as part of another group) can be straight or branched.

Carboxy$C_{1-4}$alkoxy groups are groups of structure $O(CH_2)_pCO_2R^{11}$ in which p is 1 to 4 and $R^{11}$ is hydrogen or $C_{1-4}$alkyl.

It will be appreciated that compounds of structure (I) in which one or more of $R^1$ to $R^{10}$ is a $C_{3-4}$alkyl group (either alone or as part of another group) may contain an assymetric centre due to the presence of the $C_{3-4}$alkyl group. Such compounds will exist as two (or more) optical isomers (enantiomers). Both the pure enantiomers, racemic mixtures (50% of each enantiomer) and unequal mixtures of the two are included within the scope of the present invention. Further, all diastereomeric forms possible (pure enantiomers and mixtures thereof) are within the scope of the invention.

The compounds of the present invention can be prepared by processes analogous to those known in the art, for example by:

(a) reaction of a compound of structure (II)

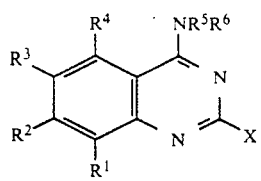

(II)

in which $R^1$ to $R^6$ are as described for structure (I) except that where necessary they are in protected form, and X is a group displaceable by an amine, with an amine of structure $R^7R^8NH$ in which $R^7$ and $R^8$ are as described for structure (I); or (b) reaction of a compound of structure (III)

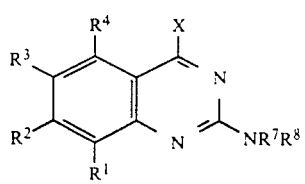

(III)

in which $R^1$ to $R^4$ and $R^7$ and $R^8$ are as described for structure (I) and X is a group displaceable by an amine, with an amine of structure $R^5R^6NH$ in which $R^5$ and $R^6$ are as described for structure (I);

(c) for compounds of structure (I) in which $NR^5R^6$ and $NR^7R^8$ are the same, reaction of a compound of structure (IV)

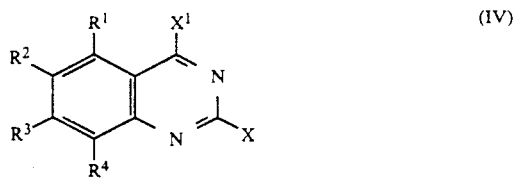

(IV)

in which $R^1$ to $R^4$ are as described for structure (II) and X and $X^1$ are both groups displaceable by an amine, with a compound of structure $R^5R^6NH$ or $R^7R^8NH$; and optionally thereafter, removing any protecting groups;

converting one group $R^1$ to $R^4$ into another group $R^1$ to $R^4$;

forming a pharmaceutically acceptable salt.

Suitable groups displaceable by an amine, X and $X^1$, will be apparent to those skilled in the art and include, for example, halogen, in particular chlorine, $SC_{1-4}$alkyl, such as methylthio, hydroxy and phenoxy.

Reaction of a compound of structure (II) with an amine $R^7R^8NH$ is suitably carried out in an inert solvent at elevated temperature. Preferably the reaction is carried out in the absence of a solvent in a sealed receptacle at elevated temperature; more preferably in an inert solvent, for example, dioxan, at reflux temperature.

Reaction of a compound of structure (III) with an amine $R^5R^6NH$ and reaction of a compound of structure (IV) with a suitable amine is suitably carried out in the presence or absence of an inert solvent at elevated temperature. Suitable solvents include, for example $C_{1-4}$alkanols such as isopropanol or butanol, preferably isopropanol, dioxan or tetrahydrofuran.

In particular, leaving groups X and $X^1$ are halogen, preferably chlorine, and can be displaced by appropriate amines $R^5R^6NH$ and $R^7R^8NH$ under the general conditions described above and in the specific examples. Other conditions and reagents depending on the nature of the leaving groups will be apparent to those skilled in the art; for example compounds of structure (I) in which $R^5$ and $R^6$ are both hydrogen, can be prepared from the corresponding compounds of structure (III) in which X is hydroxy by reaction with phenylphosphordiamidate using the method described in J. Het. Chem (1972), 9, 1235.

Pharmaceutically acceptable acid addition salts of the compounds of structure (I) can be prepared by standard procedures by, for example, reaction with suitable organic and inorganic acids the nature of which will be apparent to persons skilled in the art. For example, pharmaceutically acceptable salts can be formed by reaction with hydrochloric, sulphuric, or phosphoric acids; aliphatic, aromatic or heterocyclic sulphonic acids or carboxylic acids such as, for example, citric, maleic or fumaric acids.

Interconversions of groups $R^1$ to $R^4$ will be apparent to those skilled in the art; for example compounds in which one or more of $R^1$ to $R^4$ is other than hydroxy or hydroxy$C_{1-4}$alkyl can be carried out by alkylation of compounds of structure (I) in which one or more of $R^1$ to $R^4$ is hydroxy is carried out, for example, by reaction with a strong base, such as sodium, in a suitable solvent, such as a $C_{1-4}$alkanol, in particular ethanol, followed by treatment with a suitable alkylating agent of structure $R^{11}X^3$ in which $R^{11}$ is hydroxy$C_{1-4}$alkyl or $(CH_2)_nR^9R^{10}$ in which n, $R^9$ and $R^{10}$ are as described for structure (I), and $X^3$ is a leaving group, for example halogen, in particular chlorine or bromine. The alkylation reaction preferably is carried out in an inert solvent such as toluene, at a temperature of between ambient and reflux temperature of the solvent used, preferably at reflux temperature.

The intermediate compounds of structure (II) and (III) can be prepared by procedures analogous to those known in the art. The amines of structure $R^5R^6NH$ and $R^7R^8NH$ are available commercially or can be prepared by standard techniques well known to those skilled in the art of organic chemistry.

For example compounds of structure (II) in which $R^1$ is $OCH_3$, $R^2$ to $R^4$ are all hydrogen and X is chlorine can be prepared by the route outlined in Scheme I. It will be apparent to those skilled in the art that the reactions of Scheme 1 can also be carried out on compounds (A) in which $R^1$ to $R^4$ have different values to those indicated to produce further compounds of structure (II).

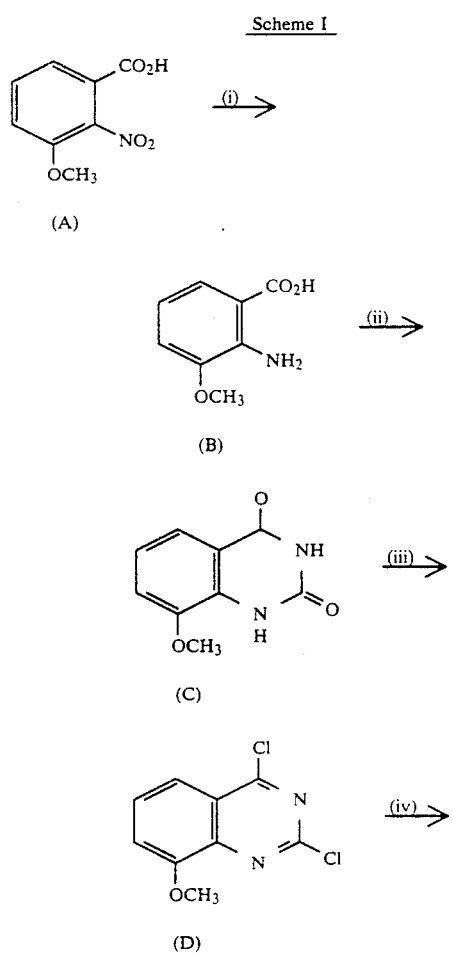

Scheme I (A)

(B)

(C)

(D)

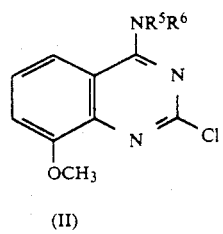

(II)

(i) $H_2$, Pd/C 10%, EtOH
(ii) KNCO, AcOH, NaOH
(iii) $POCl_3$, PhNMe$_2$, Δ
(iv) $R^5R^6NH$, NaOAc, THF/$H_2O$, Δ.

Compounds of structure (III) in which $R^7$ and $R^8$ are both hydrogen, $C_{1-4}$alkyl or $(CH_2)_nAr^1$ or one is $C_{1-4}$alkyl and the other is $(CH_2)_nAr^1$ and X is chlorine can be prepared by the procedures outlined in Scheme II. Again, it will be apparent to those skilled in the art that the reactions of Scheme (II) can be carried out on compounds (E) in which $R^1$ to $R^4$ are other than all hydrogen to product further compounds of structure (III).

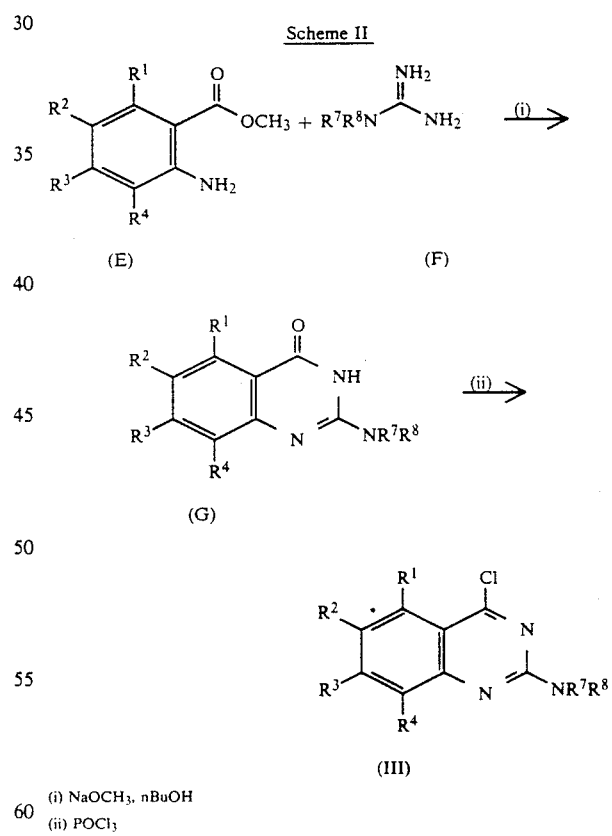

Scheme II (E)  (F)

(G)

(III)

(i) NaOCH$_3$, nBuOH
(ii) POCl$_3$

Alternatively, compounds of structure (III) can be prepared from compounds of structure (D)—see Scheme I—by the method used in J. Med. Chem., 1981, 24, 127-140.

This alternative method is outlined in Scheme III.

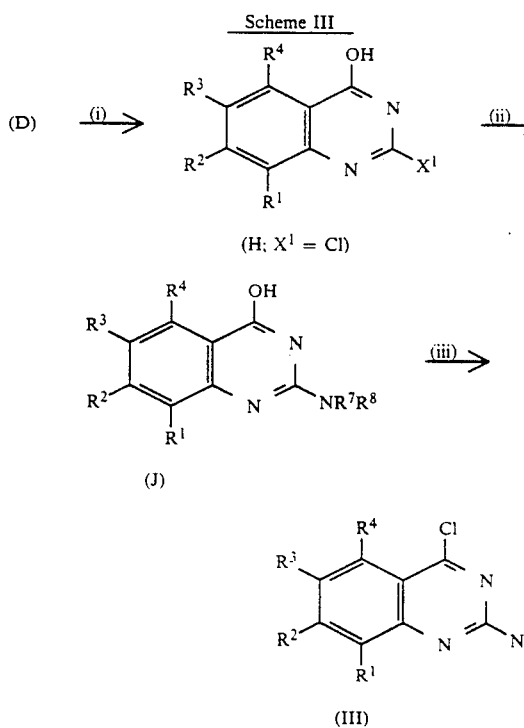

(i) NaOH/H₂O
(ii) R⁷R⁸NH, solvent, Δ
(iii) POCl₃, solvent, Δ

The starting materials used to prepare compounds of structures (II) and (III) are available commercially or can be prepared by standard techniques. In addition it will be appreciated that further variations of the above-noted schemes can be utilized, for example, in Scheme III, compounds of structure (H) in which $X^1$ is Cl can be replaced by compounds of structure (H) in which $X^1$ is, for example methylthio and then converted to compounds of structure (III) as shown. Such compounds in which $X^1$ is methylthio are prepared by standard techniques for example by treatment of the analogous thione precursor with methyl iodide in ethanol in the presence of sodium hydroxide; or, for example, when $R^1$ to $R^4$ are all H, are commercially available.

It is to be noted, and apparent to those skilled in the art that in the foregoing reactions, where necessary groups $R^1$ to $R^4$ and groups on aromatic rings Ar and $Ar^1$ (e.g. hydroxy or amino groups) will be in "protected" form. For example, amino groups can be "protected" in the form of nitro groups and converted into amino groups as appropriate, and hydroxy groups can be protected using standard groups for example as described in "Greene, T. W., Protective Groups in Organic Chemistry" which also provides examples of further appropriate protective groups for other moities.

The compounds of structure (I) and their pharmaceutically acceptable salts exert an anti-secretory effect by inhibition of the gastrointestinal H+K+ATPase enzyme (Fellenius E., Berglindh T., Sachs G., Olke L., Elander B., Sjostrand S. E., and Wallmark B., 1981, Nature, 290, 159–61), and in addition have been found to be of use as inhibitors of bone resorption.

The compounds of structure (I) and their pharmaceutically acceptable salts inhibit exogenously and endogenously stimulated gastric acid secretion and are useful in the treatment of gastrointestinal diseases in mammals, in particular humans. Such diseases include, for example, gastric and duodenal ulcers, and Zollinger-Ellison Syndrome. Further, the compounds of structure (I) can be used in the treatment of other disorders where an antisecretory effect is desirable for example in patients with gastritis, NSAID induced gastritis, gastric ulcers, acute upper intestinal bleeding, in patients with a history of chronic and excessive alcohol consumption, and in patients with gastro oesophageal reflux disease (GERD).

In addition the compounds of structure (I) have been found to be of use in medicine as inhibitors of bone resorption. In normal subjects there is a balance between bone resorption and bone formation, however, in subjects with bone affected diseases such as osteoporosis, Paget's disease and hyperparathyroidism and related disorders this balance is disturbed. As a consequence the subject suffers a loss of bone tissue, decreased bone mass and bone fragility which can result in fracturing of bones. Bone resorption (or bone loss) is associated with the activity of osteoclast cells, and it is thought that agents which inhibit the activity of such cells (and so inhibit bone resorption) will have a beneficial effect on the reduction of bone loss and be of benefit in the treatment of the above-noted disease states. The present compounds have been found to be inhibitors of osteoclast activity and bone resorption and are expected to be of use in medicine in the treatment of diseases in which bone loss is a factor, in particular osteoporosis, Paget's disease and hyperparathyroidism.

In therapeutic use, the compounds of the present invention are usually administered in a standard pharmaceutical composition. The present invention therefore provides in a further aspect pharmaceutical compositions comprising a compound of structure (I) or a pharmaceutically acceptable salt thereof and a pharmaceutically acceptable carrier.

The compounds of structure (I) and their pharmaceutically acceptable salts which are active when given orally can be formulated as liquids, for example syrups, suspensions or emulsions, tablets, capsules and lozenges.

A liquid formulation will generally consist of a suspension or solution of the compound or pharmaceutically acceptable salt in a suitable liquid carrier(s) for example, ethanol, glycerine, non-aqueous solvent, for example polyethylene glycol, oils, or water with a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

A typical suppository formulation comprises a compound of formula (I) or a pharmaceutically acceptable salt thereof which is active when administered in this way, with a binding and/or lubricating agent such as polymeric glycols, gelatins or cocoa butter or other low melting vegetable or synthetic waxes or fats.

Preferably the composition is in unit dose form such as a tablet or capsule.

Each dosage unit for oral administration contains preferably from 1 to 250 mg (and for parenteral administration contains preferably from 0.1 to 25 mg) of a compound of the formula (I) or a pharmaceutically acceptable salt thereof calculated as the free base.

The present invention also provides a method of inhibiting gastric acid secretion which comprises administering to a mammal in need thereof an effective amount of a compound of structure (IA)

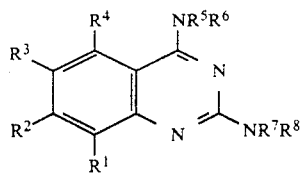

in which
R$^1$ to R$^4$ are the same or different and are each hydrogen, C$_{1-4}$alkyl, C$_{1-4}$alkoxy, phenyl, C$_{1-4}$alkylthio, C$_{1-4}$alkanoyl, amino, C$_{1-6}$alkylamino, diC$_{1-4}$alkylamino, halogen, trifluoromethyl, hydroxy, hydroxyC$_{1-4}$alkyl, carboxyC$_{1-4}$alkoxy, hydroxyC$_{1-4}$alkoxy, C$_{1-4}$alkoxyC$_{1-4}$alkoxy, O(CH$_2$)$_m$Het, C$_{1-4}$alkylNR$^9$R$^{10}$ or O(CH$_2$)$_m$NR$^9$R$^{10}$ in which m is 2 to 4 and R$^9$ and R$^{10}$ are the same or different and are each hydrogen, C$_{1-4}$alkyl, Het or —(CH$_2$)$_n$Ar where n is 0 to 4, Ar is an optionally substituted phenyl ring, m is 2 to 4 and Het is an optionally substituted heterocyclic ring, or R$^9$ and R$^{10}$ together with the nitrogen to which they are attached form a saturated or unsaturated ring optionally containing one or more further heteroatoms; provided that at least two of R$^1$ to R$^4$ are hydrogen.
R$^5$ and R$^6$ are the same, or different and are each hydrogen, C$_{1-4}$alkyl, —(CH$_2$)$_n$Ar in which n is 0 to 4 and Ar is an optionally substituted phenyl group, or R$^5$ and R$^6$ together with the nitrogen atom to which they are attached form a saturated or unsaturated ring optionally containing one or more further heteroatoms; and
R$^7$ and R$^8$ are the same or different and are each hydrogen, C$_{1-4}$alkyl, (CH$_2$)$_n$Ar$^1$ in which n is 0 to 4 and Ar$^1$ is an optionally substituted phenyl group. or R$^7$ and R$^8$ together with the nitrogen atom to which they are attached form a saturated or unsaturated ring optionally containing one or more further heteroatoms;
or a pharmaceutically acceptable salt thereof.

In addition, there is provided a method of treatment of diseases of the stomach or intestine based on increased acid secretion which comprises administering to a mammal in need thereof an effective amount of a compound of structure (IA) or a pharmaceutically acceptable salt thereof; and a method of inhibiting bone resorption which comprises administering to a mammal in need thereof an effective amount of a compound of structure (IA) or a pharmaceutically acceptable salt thereof.

The pharmaceutically acceptable compounds of the invention will normally be administered to a subject for the treatment of gastrointestinal diseases and other conditions caused or exacerbated by gastric acidity. The daily dosage regimen for an adult patient may be, for example, an oral dose of between 1 mg and 500 mg, preferably between 1 mg and 250 mg, or an intravenous, subcutaneous, or intramuscular dose of between 0.1 mg and 100 mg, preferably between 0.1 mg and 25 mg, of the compound of the formula (I) or a pharmaceutically acceptable salt thereof calculated as the free base, the compound being administered 1 to 4 times per day. Suitably the compounds will be administered for a period of continuous therapy, for example for a week or more.

In addition, the compounds of the present invention can be co-administered with further active ingredients, in particular when used to treat conditions caused or exacervated by gastric acidity. Such ingredients include antacids (for example magnesium carbonate or hydroxide and aluminium hydroxide), non-steroidal anti-flammatory drugs (for example indomethacin, aspirin or naproxen), steroids, or nitrite scavengers (for example ascorbic acid or aminosulphonic acid), or other drugs used for treating gastric ulcers (for example pirenzipine, prostanoids for example 16,16 dimethyl PGE$_2$, or histamine H$_2$-antagonists (for example, cimetidine).

The following examples illustrate the invention. Temperatures are recorded in degrees centigrade.

EXAMPLE 1

Preparation of
2-amino-8-methoxy-4-(2-methylphenylamino)quinazoline

A. Preparation of 3-methoxyanthranilic acid

2-Nitro-3-methoxybenzoic acid (10 g, 0.051 mol) was suspended in ethanol with palladium/charcoal 10% (1 g). The mixture was placed under hydrogen (50 psi) and shaken on a Parr until theoretical uptake had been achieved. The suspension was then flushed with nitrogen, the charcoal filtered off, and the filtrate evaporated in vacuo to give 3-methoxyanthranilic acid (7.76 q, 91%) m.p. 172°–175°.

B. Preparation of 8-methoxy-2,4-quinazolinedione

3-Methoxyanthranilic acid (6 g, 0.036 mol) was suspended in water (200 ml, 35°) and glacial acetic acid (2.2 ml). A freshly prepared solution of potassium cyanate (3.7 g, 0.046 mol) in water (20 ml) was added dropwise to the stirred mixture. After 2 hours, sodium hydroxide (48.5 g 1.21 mol) was added in portions keeping the temperature below 40°. A clear solution was obtained momentarily before precipitating the hydrated sodium salt. After cooling, the precipitate was filtered off, dissolved in hot water which was acidified to pH 5, causing precipitation of 8-methoxy-2,4-quinazolinedione (4.6 g, 58%) m.p. 255°–257°.

C. Preparation of 8-methoxy-2,4-dichloroquinazoline

A suspension of 8-methoxy-2,4-quinazolinedione (4 g, 0.019 mol) suspended in phosphoryl chloride (10 ml 0.108 mol) and N,N-dimethylaniline (1.6 ml, 0.0125 mol) was heated under reflux for 5 hours. The reaction mixture was poured onto ice and the precipitate washed and dried to give 8-methoxy-2,4-dichloroquinazoline (3.79 g, 87%) m.p. 155°–157°.

D. Preparation of 8-methoxy-4-(2-methylphenylamino)2-chloroquinazoline

8-Methoxy-2,4-dichloroquinazoline (3.7 g, 0.016 mol) was stirred in a mixture of water (85 ml), tetrahydrofuran (125 ml), o-toluidine (1.7 g, 0.016 mol) and sodium acetate (2.2 g, 0.027 mol) for a total of 4 days with heating to 50° for a total of 32 hours and the addition of a total of 20 ml 0.01 mol NaOH dropwise over this period maintaining the pH at 7. The reaction mixture was evaporated in vacuo and crystallised from ethanol/water to give 8-methoxy-4-(2-methylphenylamino)-2-chloroquinazoline (2.89 g, 60%) m.p. 218°–220°.

E. Preparation of 2-amino-4-(2-methylphenylamino)-8-methoxyquinazoline

8-Methoxy-4-(2-methylphenylamino)-2-chloroquinazoline (1.8 g, 0.006 mol) was dissolved in ethanolic ammonia and heated in a sealed vessel at 120° for 3 hours. After cooling, removal of excess solvent and chromatography (silica gel, 2% methanolic ammonia in chloroform) the 2 amino-4-(2-methylphenylamino)-8-methoxyquinazoline was isolated as crystals (0.52 g, 31%) from ethanol, m.p. 218°–220°.

$C_{16}H_{16}N_4O$ 0.37EtOH

Found: C 67.61, H 6.26, N 18.81.
Requires: C 67.61, H 6.17, N 18.84.

EXAMPLE 2

Preparation of 2-amino-8-methoxy-4-benzylaminoquinazoline

A. Preparation of 2-chloro-8-methoxy-4-benzylaminoquinazoline

Substituting benzylamine (1.4 g) for o-toluidine and using corresponding molar proportions in Example 1D gave, 2-chloro-8-methoxy-4-benzylaminoquinazoline (3.2 g, 82%) m.p. 253°–254°.

B. Preparation of 2-amino-8-methoxy-4-benzylaminoquinazoline

Substituting 2-chloro-8-methoxy-4-benzylaminoquinazoline (2 g, 0.0067 mol) for 2-chloro-8-methoxy-4-(2-methylphenylamino)quinazoline and using corresponding molar proportions of the other reagents in Example 1E, gave 2-amino-8-methoxy-4-benzylaminoquinazoline (0.29 g, 15%) from ethanol, m.p. 243°–245°.

$C_{16}H_{16}N_4O$

Found: C68.77, H 5.52, N 20.16.
Requires: C 68.55, H 5.75, N 19.99.

EXAMPLE 3

Preparation of 2-amino-8-methoxy-4-(2-methyl-4-methoxyphenylamino)quinazoline

A. Preparation of 2-chloro-8-methoxy-4-(2-methyl-4methoxyphenylamino)quinazoline Substituting 4-methoxy-o-toluidine (1.6 g, 0.0122 mol) for o-toluidine and using corresponding molar proportions of the other reagents in Example 1D, gave 2-chloro-8-methoxy-4-(4-methoxy-2-methylphenylamino)quinazoline (2.02 g, 51%) m.p. 230°–232°.

B. Preparation of 2-amino-8-methoxy-4-(2-methyl-4-methoxyphenylamino)quinazoline Substituting 2-chloro-8-methoxy-4-(2-methyl-4-methoxyphenylamino)quinazoline (2.0 g, 0.006 mol) for 2-chloro-8-methoxy-4-(2-methylphenylamino)quinazoline and using corresponding molar proportions of the other reagents in the Example 1E, gave 2-amino-8-methoxy-4-(2-methyl-4-methoxyphenylamino)quinazoline (0.25 g, 13%) from ethanol/water, m.p. 185°–187°.

$C_{17}H_{18}N_4O_2$ 0.5 $H_2O$

Found: C 63.95, H 5.77, N 17.52.
Requires: C 63.93, H 5.99, N 17.54.

EXAMPLE 4

Preparation of 2-amino-8-methoxy-4-(2-methylbenzylamino)quinazoline

A. Preparation of 2-chloro-8-methoxy-4-(2-methylbenzylamino)quinazoline

Substituting 2-methylbenzylamine for o-toluidine (1.41 g, 0.0117 mol) and using corresponding molar proportions of the other reagents in the Example 1D, gave 2-chloro-8-methoxy-4-(2-methylbenzylamino)-quinazoline (3.36 g, 89%) m.p. 279°–281°.

B. Preparation of 2-amino-8-methoxy-4-(2-methylbenzylamino)quinazoline

Substituting 2-chloro-8-methoxy-4-(2-methylbenzylamino)quinazoline (2.3 g, 0.0073 mol) for 2-chloro-8-methoxy-4-(2-methylphenylamino)quinazoline in Example 1E, gave 2-amino-8-methoxy-4-(2-methylbenzylamino)quinazoline (0.4 g, 18.5%) from acetonitrile, m.p. 274°–275°.

$C_{17}H_{18}N_4O$ 0.67 $H_2O$ 0.36$CH_3CN$

Found: C 68.78, H 6.20, N, 19.07.
Requires: C 69.03, N 6.19, N, 19.03.

EXAMPLE 5

Preparation of 2-dimethylamino-8-methoxy-4-(2-methylphenylamino)-quinazoline

A. Preparation of 2-dimethylamino-8-methoxy-4-(2-methylphenylamino)-quinazoline

Substituting ethanolic dimethylamine for ethanolic ammonia and using corresponding molar proportions of the other reagents in the Example 1E, gave 2-dimethylamino-8-methoxy-4-(2-methylphenylamino)-quinazoline (0.73 g, 59%) from acetonitrile, m.p. 141°–143°.

$C_{18}H_{20}N_4O$ 0.2 $H_2O$

Found: C 69.37, H 6.34, N 18.01.
Requires: C 69.30, H 6.59, N 17.96.

EXAMPLE 6

Preparation of 2-amino-8-methyl-4-(2-methylphenylamino)quinazoline

A. Preparation of 8-methyl-2,4-quinazolone

Substituting 3-methylanthranilic acid (5 g, 0.033 mol) for 3-methoxyanthranilic acid and using corresponding molar proportions of the other reagents in Example 1B gave 8-methyl-2,4-quinazolinedione (4.18 g, 72%), m.p. 285°–287°.

B. Preparation of 2,4-dichloro-8-methylquinazoline

Substituting 8-methyl-2,4-quinazolinedione (4.0 g, 0.023 mol) for 8-methoxy-2,4-quinazolinedione and using corresponding molar proportions of the other reagents in Example 1C, gave 2,4-dichloro-8-methylquinazoline (4.12 g, 84%), m.p. 180°–230° which was used without further purification.

C. Preparation of 2-chloro-8-methyl-4-(2-methylphenylamino)quinazoline

Substituting 2,4-dichloro-8-methyl-4-(2-methylphenylamino)quinazoline (3.7 g, 0.018 mol) for 2,4-dichloro-8-methoxyquinazoline and using corresponding molar proportions of the other reagents in Example 1D, gave 2-chloro-8-methyl-4-(2-methylphenylamino)quinazoline (3.96 g, 77%), m.p. 125°–126°.

D. preparation of 2-amino-8-methyl-4-(2-methylphenylamino)quinazoline

Substituting 2-chloro-8-methyl-4-(2-methylphenylamino)quinazoline (2.0 g, 0.007 mol) for 2-chloro-8-methoxy-4-(2-methylphenylamino)quinazoline and using corresponding molar proportions of the other reagents in Example 1E, gave 2-amino-8-methyl-4-(2-methylphenylamino)quinazoline (0.27 g, 15.3%) from acetonitrile/water, m.p. 118°–120°.

$C_{16}H_{16}N_4$

Found: C 72.59, H 6.21, N 21.17.
Requires: C 72.70, H 6.10, N 21.20.

EXAMPLE 7

Preparation of 2-amino-4-(2-methylphenylamino)quinazoline

A. Preparation of 2-amino-4-(3H)-quinazolone

Guanidine hydrochloride (47.77 g, 0.5 mol) was added portionwise to a stirred suspension of sodium methoxide (32.42 g, 0.60 mol) in n-butanol (450 ml) at ambient temperature over 0.5 hour. After a further 0.5 hour a solution of methyl anthranilate (15 g, 0.10 mol) in n-butanol (150 ml) was added dropwise and then slowly brought to reflux. After distilling off ca. 100 ml of solvent the reaction mixture was heated under reflux at 116° for 117 hours. The cooled suspension was filtered, excess solvent removed and the residue dissolved in water, acidified to pH 5 and extracted with diethyl ether. The aqueous suspension was reacidified to pH 5, filtered off, washed with water and dried. The solid was then triturated in methanol, filtered, washed with ether and dried to give 2-amino-4-(3H)-quinazolone (3.0 g, 19%) m.p. >300°.

B. Preparation of 2-amino-4-chloroquinazoline

2-Amino-4-(3H)-quinazolone (2.0 g, 0.0124 mol) was heated under reflux in phosphoryl chloride (19.02 g, 0.0124 mol) for 2.5 hours. The reaction mixture was partitioned between chloroform, ice and NaOH solution (pH 9) and the organic phase dried, filtered, excess solvent removed and the residue triturated with chloroform to give 2-amino-4-chloroquinazoline (0.42 g, 19%) m.p. 275°–278°.

C. Preparation of 2-amino-4-(2-methylphenylamino)quinazoline

2-Amino-4-chloroquinazoline (0.64 g, 0.0036 mol) was heated to 170° in o-toluidine (1 ml, 0.008 mol) for 1 hour. The reaction mixture was dissolved in ethanol, stripped and partitioned between chloroform and NaOH solution (pH 9). The organic solution was dried, filtered and excess solvent removed to give an oil which afforded crystals of 2-amino-4-(2-methylphenylamino)-quinazoline (0.55 g, 62%) m.p. 273°–275° (from ethanol).

$C_{15}H_{14}N_4$ 0.002$CHCl_3$

Found: C 71.08, H 5.42, N 22.04.
Requires: C 71.36, H 5.59, N 22.16.

EXAMPLE 8

Preparation of 2-pyrrolidino-4-(2-methylphenylamino)quinazoline

A. Preparation of 2-chloro-4-(2-methylphenylamino)quinazoline

Substituting 2,4-dichloroquinazoline (9.95 g, 0.05 mol) for 8-methoxy-2,4-dichloroquinazoline and using corresponding molar proportions of the other reagents in Example 1D, gave 2-chloro-4-(2-methylphenylamino)quinazoline (10.19 g, 76%) m.p. 192°–194°.

B. Preparation of 2-pyrrolidino-4-(2-methylphenylamino)quinazoline 2-chloro-4-(2-methylphenylamino)quinazoline (5 g, 0.0185 mol) and pyrrolidine (6.59 g, 0.093 mol) were dissolved in ethanol (65 ml) placed in a sealed vessel and heated to 135° for 5 hours. After cooling, the reaction mixture was dissolved in ethanol and then evaporated in vacuo. The oily residue afforded crystals of 2-pyrrolidino-4-(2-methylphenylamino)quinazoline (3.67 g, 65%) from ethanol/water, m.p. 152°–154°.

$C_{19}H_{20}N_4$

Found: C 74.58, H 6.60, N 18.49.
Requires: C 74.97, H 6.62, N 18.41.

EXAMPLE 9

Preparation of 2-ethylamino-4-(2-methylphenylamino)quinazoline

2-Chloro-4-(2-methylphenylaminomethyl)quinazoline (5.00 g, 0.0185 mol) and ethylamine in ethanol (33%, 30 ml) were dissolved in ethanol (35 ml) placed in a sealed vessel and heated for 5 hours at 130°. After cooling and removal of excess solvent in vacuo the residue afforded crystals of 2-ethylamino-4-(2-methylphenylamino)quinazoline (1.7 g, 33%) from ethanol/water, m.p. 127°–129°.

$C_{17}H_{18}N_4$

Found: 73.09, H 6.43, N 20.06.
Requires: C 73.35, H 6.52, N 20.13.

EXAMPLE 10

Preparation of 2-benzylamino-4-(2-methylphenylamino)quinazoline

2-Chloro-4-(2-methylphenylamino)quinazoline (2.7 g, 0.01 mol) and benzylamine (2.4 g, 0.022 mol) were dissolved in n-butanol (20 ml) and heated under reflux for 5 hours. The solution was cooled, excess solvent removed in vacuo and the residue treated with water, filtered and crystallised from ethanol/water. The compound was then chromatographed (silica gel, 0.5% methanolic ammonia/chloroform) to afford an oil, which on trituration with ether gave crystals of 2-benzylamino-4-(2-methylphenylamino)quinazoline (1.88 g, 55%), m.p. 127°–130°.

$C_{22}H_{20}N_4$

Found: C 77.50, H 6.00, N 16.45.
Requires: C 77.62, H 5.92, N 16.46.

EXAMPLE 11

Preparation of 2-amino-4-(2-methylphenylamino)-6-ethylquinazoline

A. Preparation of 6-ethyl-2,4-quinazoline dione

Substituting 6-ethylanthranilic acid for 3-methoxyanthranilic acid and using corresponding molar proportions of the other reagents in Example 1B, gave 6-ethyl-2,4-quinazoline dione (20.15 g, 90%) m.p. 325°.

B. Preparation of 6-ethyl-2,4-dichloroquinazoline

Substituting 6-ethyl-2,4-quinazolinedione (20 g, 0.105 mol) for 8-methoxy-2,4-quinazolinedione and using corresponding molar proportions of the other reagents in Example 1C, gave 6-ethyl-2,4-dichloroquinazoline (19.57 g, 82%) m.p. 90°–92°.

C. Preparation of 2-chloro-4-(2-methylphenylamino)6-ethylquinazoline

Substituting 6-ethyl-2,4-dichloroquinazoline (10.0 g, 0.044 mol) for 8-methoxy-2,4-dichloroquinazoline and using corresponding molar proportions of the other reagents in Example 1D, gave 2-chloro-4-(2-methylphenylamino)-6-ethylquinazoline (7.23 g, 56%) m.p. 177°–179°.

D. Preparation of 2-amino-4-(2-methylphenylamino)-6ethylquinazoline

Substituting 2-chloro-4-(2-methylphenylamino)-6-ethylquinazoline (2.98 g, 0.01 mol) for 8-methoxy-2-chloro-4-(2-methylphenylamino)quinazoline and using corresponding molar proportions of the other reagents in Example 1E, gave 2-amino-4-(2-methylphenylamino)-6-ethylquinazoline (0.76 g, 27%) from ether, m.p. 263°–265°.

$C_{17}H_{18}N_4$ 1.5% w/w $CHCl_3$

Found: C 72.18, H 6.49, N 19.76.
Requires: C 72.40, H 6.43, N 19.83.

EXAMPLE 12

Preparation of 8-methoxy-2.4-bis(2-methylphenylamino)quinazoline 8-methoxy-4-(2-methylphenylamino)-2-chloroquinazoline (1.00 g, 0.0033 mol) was dissolved in ethanol (15 ml) with o-toluidine (1.06 g, 0.0099 mol) and heated in a sealed vessel at 150° for 5 hours. After cooling and removal of excess solvent in vacuo the solid was chromatographed (silica gel, chloroform). 8-Methoxy-2,4-bis(2-methylphenylamino)quinazoline was isolated as crystals (0.93 g, from ethanol/water, m.p. 185°–187°.

$C_{23}H_{22}N_4O$

Found: 74.48, H 6.00, N 14.92.
Requires: C 74.57, H 5.99, N 15.12.

EXAMPLE 13

Preparation of 2-methylamino-8-methoxy-4-(2-methylphenylamino)-quinazoline

Substituting ethanolic methylamine for ethanolic ammonia and using corresponding molar proportions of the other reagents in the Example 1E, gave 2-methylamino-8-methoxy-4-(2-methylphenylamino)-quinazoline (0.3 g, 35%) from ethanol/water, m.p. 190°–192°.

$C_{17}H_{18}N_4O$

Found: C 69.24, H 6.07, N 18.81.
Requires: C 69.37, H 6.16, N 19.04.

EXAMPLE 14

Preparation of 2-benzylamino-8-methoxy-4-(2-methylphenylamino)-quinazoline

Substituting benzylamine (0.53 g 0.00495 mol) for o-toluidine and using corresponding molar proportions of the other reagents in Example 12 gave 2-benzylamino-8-methoxy-4-(2-methylphenylamino)quinazoline hydrochloride (0.62 g, 46%) from ethanolic HCl, m.p. 237°–238°.

C₂₃H₂₂N₄O.HCl 0.5 H₂O

Found: C 65.65, H 5.69, N 13.41, Cl 8.3.
Requires: C 67.42, H 5.81, N 13.47, Cl 8.52.

EXAMPLE 15

Preparation of 2-pyrrolidino-8-methoxy-4-(2-methylphenyl amino)quinazoline

Substituting pyrrolidine (2.1 g, 0.03 mol) for o-toluidine and using corresponding molar proportions of the other reagents in Example 12 gave 2-pyrrolidino-8-methoxy-4-(2-methylphenylamino)quinazoline (1.71 g, 77%) from ethanol, m.p. 181°–183°.

C₂₀H₂₂N₄O

Found: C 71.55, H 6.75, N 16.60.
Requires: C 71.83, H 6.63, N 16.75.

EXAMPLE 16

Preparation of 2-phenylethylamino-4-(2-methylphenylamino)quinazoline

Substituting phenylethylamine (3.64 g, 0.03 mol) for benzylamine and using corresponding molar proportions of the other reagents in Example 10 and using ethanol as the solvent gave 2-phenylethylamino-4-(2-methylphenylamino)quinazoline (1.45 g, 58%) from ether, m.p. 95°–96°.

C₂₃H₂₂N₄ 0.15 H₂O

Found: C 77.39, H 6.24, N 15.71.
Requires: C 77.34, H 6.29, N 15.68.

EXAMPLE 17

Preparation of 8-methyl-4-(2-methylphenylamino)-2-(2-phenylethylamino)quinazoline hydrochloride 8-Methyl-4-(2-methylphenylamino)-2-chloroquinazoline (0.71 g, 0.0025 mol) was dissolved in ethanol (20 ml) with 2-phenylethylamine (0.61 g, 0.005 mol) and heated in a sealed vessel at 140° for 4 hours. After cooling and removal of excess solvent in vacuo the glass was dissolved in a small amount of methanol and 2N HCl added to form the hydrochloride salt which was recrystallised from ethanol/ether to give 8-methyl-4-(2-methylphenylamino)-2-(2-phenylethylamino)quinazoline hydrochloride (0.5 g, 50%), m.p. >250°.

C₂₄H₂₄N₄ 1.0HCl

Found: C 71.28, H 6.35, N 13.82, Cl 8.77.
Requires: C 71.18, H 6.22, N 13.84, Cl 8 76.

EXAMPLE 18

Preparation of 2-amino-8-methoxy-4-(2-methoxyphenylamino)quinazoline

A. Preparation of 2-chloro-8-methoxy-4-(2-methoxyphenylamino)quinazoline

Substituting o-anisidine (2.94 g) for o-toluidine and using corresponding molar proportions of the other reagents in Example 1D gave, 2-chloro-8-methoxy-4-(2-methoxyphenylamino)quinazoline (6.74 g, 98%) m.p. 194°–196°.

B. Preparation of 2-amino-8-methoxy-4-(2-methoxyphenylamino)quinazoline

Substituting 2-chloro-8-methoxy-4-(2-methoxyphenylamino)quinazoline (4.0 g) for 2-chloro-8-methoxy-4-(2-methylphenylamino)quinazoline and using corresponding molar proportions of the other reagents in Example 1E gave, after recrystallisation from ethanol/water 2-amino-8-methoxy-4-(2-methoxyphenylamino)quinazoline (0.16 g, 4.2%), m.p. 243°–244°.

C₁₆H₁₆N₄O₂ 0.18 H₂O

Found: C 63.88, H 5.38, N 18.87.
Requires: C 64.14, H 5.50, N 18.70.

EXAMPLE 19

Preparation of 2,4-Bis-(N-methylphenylamino)-8-methoxyquinazoline

8-Methoxy-2,4-dichloroquinazoline (1.5 g, 0.007 mol) was heated under reflux in a solution of N-methyl aniline (1.43 m), 0.014 mol) in tetrahydrofuran (50 ml) for 16 hours precipitating a solid, which was collected and crystallised from ethanol/water to give 2,4-bis-(N-methylphenylamino)-8-methoxyquinazoline (0.37 g, 15%), m.p. 169°–170°.

C₂₃H₂₂N₄O

Found: C 74.32, H 5.85, N 15.04.
Requires: C 74.57, H 5.99, N 15.12.

EXAMPLE 20

Preparation of 2,4-Bis-(N-methylphenylamino)quinazoline hydrochloride

Substituting 2,4-dichloroquinazoline (4.5 g, 0.0226 mol) for 8-methoxy-2,4-dichloroquinazoline and using corresponding molar proportions of the other reagents in Example 20, gave after crystallisation from ethanolic hydrogen chloride 2,4-bis-(N-methylphenylamino)quinazoline hydrochloride (2.2 g, 30%), m.p. 243°–244°.

C₂₂H₂₀N₄ 1.0 HCl

Found: C 69.79, H 5.56, N 14.72, Cl 9.02.
Requires: C 69.89, H 5.70, N 14.68, Cl 9.29.

EXAMPLE 21

Preparation of 2-(N-methylphenylamino)-4-(2-methylphenylamino)-8-methoxyquinazoline Substituting N-methylaniline (1.4 g, 0.013 mol) for o-toluidine and using the corresponding molar proportions of the other reagents in Example 12 gave after crystallisation from ethanol 2-(N-methylphenylamino)-4-(2methylphenylamino)quinazoline (0.45 g, 45%), m.p. 145°–147°.

$C_{23}H_{22}N_4O$

Found: C 74.89, H 6.10, N 15.34.
Requires: C 74.57, H 5.99, N 15.12.

EXAMPLE 22

Preparation of 2-(N-methylphenylamino)-4-(2-methylphenylamino)-quinazoline hydrochloride Substituting N-methylaniline (2.39 g, 0.022 mol) for benzylamine and using corresponding molar proportions of the other reagents in Example 10 and using ethanol as the solvent gave after crystallisation from ethanolic hydrogen chloride 2-(N-methylphenylamino)-4-(2-methylphenylamino)quinazoline hydrochloride (1.64 g, 39%), m.p. 284°–286°.

$C_{22}H_{20}N_4$ 1.0 HCl

Found: C 70.06, H 5.73, N 14.83, Cl 9.17.
Requires: C 70.11, H 5.62, N 14.87, Cl 9.41.

EXAMPLE 23

Preparation of 2-phenethylamino-4-(2-methylphenylamino)8-methoxyquinazoline hydrochloride Substituting phenylethylamine (1.2 ml, 0.009 mol) for o-toluidine and using corresponding molar proportions of the other reagents in Example 12, gave after crystallisation from ethanolic hydrogen chloride/ether 2-phenethylamino-4-(2-methylphenylamino)-8-methoxyquinazolinehydrochloride (0.38 g, 42%), m.p. 263°–265°.

$C_{24}H_{24}N_4O$ 1.0 HCl

Found: C 68.62, H 6.06, N 13.64, Cl 8.22.
Requires: C 68.48, H 5.99, N 13.31, Cl 8.42.

EXAMPLE 24

Preparation of 4-(N-methylphenylamino)-2-(2-methylphenylamino)-8-methoxyquinazoline A. Preparation of 8-methoxy-4-(N-methylphenylamino)-2-chloroquinazoline Substituting N-methylaniline (3.85 g, 0.036 mol) for o-toluidine and using corresponding molar proportions of the other reagents in Example 1D, gave after crystallisation from ethanol/water 8-methoxy-4-(N-methylphenylamino)-2-chloroquinazoline (6.19 g, 63%), m.p. 115°–117°.

B. Preparation of 8-methoxy-4-(N-methylphenylamino)2-(2-methylphenylamino)quinazoline hydrochloride Substituting 8-methoxy-4-(N-methylphenylamino)-2-chloroquinazoline (1.5 g, 0.005 mol) for 8-methoxy-4-(2-methylphenylamino)-2-chloroquinazoline and using corresponding molar proportions of the other reagents in Example 12, gave after crystallisation from ethanolic hydrogen chloride/ether 4-(N-methylphenylamino)-2-(2-methylphenylamino)-8-methoxyquinazoline hydrochloride (0.99 g, 49%), m.p. 232°–234°.

$C_{23}H_{22}N_4O$ 1.0 HCl

Found: C 67.74, H 5.63, N 13.76, Cl 8.39.
Requires: C 67.89, H 5.70, H 13.77, Cl, 8.71.

EXAMPLE 25

Preparation of 2-amino-4-(2-methylbenzylamino)quinazoline

A. Preparation of 2-chloro-4-(2-methylbenzylamino)quinazoline 2,4-Dichloroquinazoline (3.0g 0.015 mol) was stirred in a mixture of water (60 ml), tetrahydrofuran (100 ml), o-methylbenzylamine (1.83 g, 0.015 mol) and sodium acetate (1.38 g, 0.017 mol) for a total of 16 hours. The reaction mixture was evaporated under reduced pressure and crystallised from ethanol to give 2-chloro-4-(2-methylbenzylamino)quinazoline (1.44 g, 30%), m.p. 215°–217°.

B. Preparation of 2-amino-4-(2-methylbenzylamino)quinazoline hydrochloride

Substituting 2-chloro-4-(2-methylbenzylamino)-quinazoline (1.3 g, 0.004 mol) for 2-chloro-4-(2-methylphenylamino)-8-methoxyquinazoline and using corresponding molar proportions of the other reagents in the Example 1E gave after crystallisation from ethanolic hydrogen chloride/ether 2-amino-4-(2-methylbenzylamino)quinazoline hydrochloride (0.5 g, 42%), m.p. 258°–260°.

$C_{16}H_{16}N_4$ 1.0 HCl 0.1 $H_2O$

Found: C 63.41, H 5.69, N 18.54, Cl 11.90.
Requires: C 63.51, H 5.73, N 18.51, Cl 11.71.

EXAMPLE 26

Preparation of 2-(2-methylphenylamino)-4-(N-methylphenylamino)-quinazoline hydrochloride A. Preparation of 2-chloro-4-(N-methylphenylamino)quinazoline Substituting N-methylphenylamine (9.9 g, 0.092 mol) for 2-methyl-benzylamine and using corresponding molar proportions of the other reagents in Example 25A, gave after crystallisation from ethanol/water 2-chloro-4-(N-methylphenylamino)quinazoline hydrochloride (24.47 g, 75%), m.p. >300°.

B. Preparation of 2-(2-methylphenylamino)-4-(N-methylphenylamino)-quinazoline hydrochloride Substituting 2-chloro-4-(N-methylphenylamino)-quinazoline (2.0 g, 0.007 mol) for 2-chloro-8-methoxy-4-(2-methylphenylamino)quinazoline and using corresponding molar proportions of the other reagents in Example 12, gave after crystallisation from ethanolic hydrogen chloride 2-(2-methylphenylamino)-4-(N-methylphenylamino)quinazoline hydrochloride (1.36 g, 48%), m.p. 255°–257°.

$C_{22}H_{20}N_4$ 1.0 HCl

Found: C 69.95, H 5.58, N 14.89, Cl 9.38.
Requires: C 70.11, H 5.62, N 14.87, Cl 9.41.

EXAMPLE 27

Preparation of 2-phenylamino-4-(N-methylphenylamino)quinazoline hydrochloride

2-Chloro-4-(N-methylphenylamino)quinazoline (2.0 g, 0.007 mol) was dissolved in ethanol (20 ml) with aniline (1.37 g, 0.15 mol) and heated in a sealed vessel at 150° for 5 hours. After cooling and removal of excess solvent in vacuo pressure the solid was treated with ethanolic hydrogen chloride to form the hydrochloride which was recrystallised from ethanol to give 2-phenylamino-4-(N-methylphenylamino)quinazoline hydrochloride (1.99 g, 74%), m.p. 265°–267°.

$C_{21}H_{18}H_4$ 1.0 HCl

Found: C 69.28, H 5.17, N 15.35, Cl 9.78.
Requires: C 69.51, H 5.28, N 15.44, Cl 9.77.

EXAMPLE 28

Preparation of 2-amino-4-(N-methylphenylamino)quinazoline hydrochloride

Substituting N-methylaniline (1.95 g, 0.0183 mol) for O-toluidine and using corresponding molar proportions of the other reagents in Example 7C, gave after crystallisation from ethanolic hydrogen chloride 2-amino-4-(N-methylphenylamino)quinazoline hydrochloride (0.27 g, 13%), m.p. 190°–192°.

$C_{15}H_{14}N_4$ 0.3 $H_2O$ 0.15 HCl

Found: C 68.43, H 5.48, N 21.59, Cl 2.17.
Requires: C 68.81, H 5.70, N 21.40, Cl 2.04.

EXAMPLE 29

Preparation of 2-amino-4-(N-methylphenylamino)-8-methoxyquinazoline hydrochloride Substituting 2-amino-4-chloro-8-methoxyquinazoline for 2-amino-4-chloroquinazoline and using corresponding molar proportions of the other reagents in Example 28, gave after crystallisation from ethanolic hydrogen chloride 2-amino-4-(N-methylphenylamino)-8-methoxyquinazoline hydrochloride (0.27 g, 10%), m.p. 282°–284°.

$C_{16}H_{16}N_4O$ HCl

Found: C 60.34, H 5.60, N 17.67, Cl 10.98.
Requires: C 60.66, H 5.38, N 17.69, Cl 11.19.

EXAMPLE 30

Preparation of 2-(4-hydroxy-2-methylphenyl)amino1-4-(N-methylphenylamino) quinazoline hydrochloride Substituting 4-hydroxy-2-methylaniline (1.8 g 0.0148 mol) for aniline and using corresponding molar proportions of the other reagents in Example 27, gave after crystallisation from ethanolic hydrogen chloride 2-[(4-hydroxy-2-methylphenyl)amino]quinazoline hydrochloride (0.72 g, 24%), m.p. 274°–276°.

$C_{22}H_{20}N_4O$ 1.0 HCl

Found: C 66.91, H 5.33, N 14.06, Cl 8.97.
Requires: C 67.25, H 5.39, N 14.26, Cl 9.02.

EXAMPLE 31

Preparation of 2-(2-methylbenzylamino)-4-(N-methylphenylamino)-quinazoline hydrochloride Substituting 2-methylbenzylamine (1.79 g, 0.0148 mol) for aniline and using corresponding molar proportions of the other reagents in Example 27, gave after crystallisation from ethanolic hydrogen chloride 2-(2-methylbenzylamino)-4-(N-methylphenylamino)-quinazoline hydrochloride (0.61 g, 21%), m.p. 226°–228°.

$C_{23}H_{22}N_4$ 1.0 HCl

Found: C 70.44, H 5.90, N 14.36, Cl 9.08.
Requires: C 70.67, H 5.93, N 14.33, Cl 9.07.

EXAMPLE 32

Preparation of 2-(2-methyl-4-fluorophenyl)amino]-4-(N-methylphenylamino)quinazoline hydrochloride Substituting 2-methyl-4-fluoroaniline (1.85 g, 0.0148 mol) for aniline and using corresponding molar proportions of the other reagents in Example 27, gave after crystallisation from ethanolic hydrogen chloride 2-[(2-methyl-4-fluorophenyl)amino]-4-(N-methylphenylamino)quinazoline hydrochloride (0.6 g, 15%), m.p. 243°–245°.

$C_{22}H_{19}N_4F$ 1.0 HCl

Found: C 66.50, H 5.24, N 14.17, Cl 8.93.
Requires: C 66.92, H 5.11, N 14.19, Cl 8.98.

EXAMPLE 33

Preparation of 2-(2-methylphenylamino)-4-phenylaminoquinazoline hydrochloride

A. Preparation of 2-(2-methylphenylamino)-4-quinazolone

2-Methylthio-4-quinazolone (10.0 g, 0.052 mol) was fused with o-toluidine (8.35 g, 0.078 mol) at 160°. After 4 hours, the solid was treated with ethanol, and filtered to give 2-methylphenylamino-4-quinazolone (10.7 g, 82%) m.p. 278°–280°.

B. Preparation of 4-chloro-2-(2-methylphenylamino)quinazoline 2-(2-Methylphenylamino)-4-quinazolone (5.0 g, 0.0198 mol) was dissolved in phosphoryl chloride (20 ml, 0.216 mol) and N,N-dimethylaniline (3.5 ml, 0.025 mol) and refluxed for ¾ hours. The reaction mixture was poured onto ice/N NaoH (100 ml) and the precipitate washed and dried to give 4-chloro-2-(2-methylphenylamino)quinazoline hydrochloride (5.79 g, 95%), used without purification.

C. Preparation of 2-(2-methylphenylamino)-4-phenylaminoquinazoline hydrochloride 4-Chloro-2-(2-methylphenylamino)quinazoline (1.5 g, 0.0048 mol) was dissolved in aniline (1.5 ml, 0.016 mol) and heated at 170° for 1 hour. After cooling and evaporation of excess solvent the residue was crystallised from ethanolic hydrogen chloride to give 2-(2-methylphenylamino)-4-phenylaminoquinazoline hydrochloride (0.30 g, 17%) m.p. 239°-240°.

$C_{21}H_{18}N_4$ 1.0 HCl 0.19 $H_2O$ 0.02 EtOH

Found: C 68.96, H 5.31, N 15.42, Cl 9.59.
Requires: C 68.71, H 5.37, N 15.22, Cl 9.63.

EXAMPLE 34

Preparation of 2-(2-methylphenylamino)-4-methylaminoquinazoline hydrochloride 2-(2-methylphenylamino)-4-chloroquinazoline (2 g, 0.0065 mol) and methylamine in ethanol (33%, 30 ml) were placed in a pressure vessel and heated for 4 hours at 140°. After cooling, the reaction mixture was evaporated to dryness. The residue afforded crystals of 2-(2-methylphenylamino)-4-methylaminoquinazoline hydrochloride (0.29 g, 8.9%) from ethanolic hydrogen chloride, m.p. 275°-279°.

$C_{16}H_{16}N_4$ HCl

Found: C 63.70, H 5.56, N 18.58, Cl 11.76.
Requires. C 63.89, H 5.70, N 18.63, Cl 11.79.

EXAMPLE 35

Preparation of 2-(2-methylphenylamino)-4-propylaminoquinazoline hydrochloride

Substituting n-propylamine (1.77 g, 0.03 mol) for methylamine and using corresponding molar proportions of the other reagents in Example 34, gave after crystallisation 2-(2-methylphenylamino)-4-propylaminoquinazoline hydrochloride (0.67 g, 20.5%) from ethanolic hydrogen chloride, m.p. 215°-217°.

$C_{17}H_{18}N_4$ HCl

Found: C 65.12, H 6.20, N 17.83, Cl 11.20.
Requires: C 64.86, H 6.08, N 17.80, Cl 11.26.

EXAMPLE 36

Preparation of 2-(2-methylphenylamino)-4-(n-pentylamino)quinazoline hydrochloride Substituting amylamine (1.13 g, 0.013 mol) for methylamine and using corresponding molar proportions of the other reagents in Example 34, gave after crystallisation 2-(2-methylphenylamino)-4-(n-pentylamino)quinazoline hydrochloride (0.24 g, 10.3%) from ethanolic hydrogen chloride/ether, m.p. 129°-130°.

$C_{20}H_{24}N_4$ HCl

Found: C 67.37, H 7.19, N 15.46, Cl 9.86.
Requires: C 67.31, H 7.06, N 15.70, Cl 9.93.

EXAMPLE 37

Preparation of 2-(2-methylphenylamino)-4-(2-methoxybenzylamino)quinazoline hydrochloride Substituting 2-methoxybenzylamine (1.78 g, 0.0147 mol) for methylamine and using corresponding molar proportions of the other reagents in Example 34, gave after crystallisation 2-(2-methylphenylamino)-4-(2-methoxybenzylamino)quinazoline hydrochloride (1.52 g, 7.5%) from ethanolic hydrogen chloride, m.p. 218°-220°.

$C_{23}H_{22}N_4O$ HCl

EXAMPLE 38

Preparation of 2-(2-methylphenylamino)-4-N-piperidinoquinazoline hydrochloride

Substituting piperidine (1.25 g, 0.0147 mol) for methylamine and using corresponding molar proportions of the other reagents in Example 34, gave after crystallisation 2-(2-methylphenylamino)-4-N-piperidinoquinazoline hydrochloride (0.25 g, 10%) from ethanolic hydrogen chloride/ether, m.p. 218°-220°.

$C_{20}H_{22}N_4$ HCl

Found: C 67.48, H 6.51, N 15.63, Cl 9.94.
Requires: C 67.69, H 6.53, N 15.79, Cl 9.99.

EXAMPLE 39

Preparation of 2-(2-methylphenylamino)-4-N-morpholinoquinazoline hydrochloride

Substituting morpholine (1.28 g, 0.0147 mol) for methylamine and using corresponding molar proportions of the other reagents in Example 34, gave after crystallisation 2-(2-methylphenylamino)-4-N-morpholinoquinazoline hydrochloride (0.26 g, 11.2%), from ethanolic hydrogen chloride/ether, m.p. 244°-246°.

$C_{19}H_{20}N_4O$ HCl

Found: C 64.04, H 6.03, N 15.80, Cl 10.04.
Requires: C 63.95, H 5.93, N 15.70, Cl 9.94.

EXAMPLE 40

Preparation of 2-(2-methylphenylamino)-4-dimethylaminoquinazoline hydrochloride

Substituting dimethylamine (30 ml) for methylamine and using corresponding molar proportions of the other reagents in Example 34, gave after crystallisation 2-(2- methylphenylamino)-4-dimethylaminoquinazoline hydrochloride (0.29 g, 11.8%), m.p. 277°-282° decomp.

$C_{17}H_{18}N_4$ HCl

Found: C 65.10, H 6.20, N 17.83, Cl 11.20.
Requires: C 64.86, H 6.08, N 17.80, Cl 11.26.

EXAMPLE 41

Preparation of
2-(2-methyl-4-fluorophenylamino)-4-(N-methylphenylamino)-8-methoxyquinazoline hydrochloride 2-Chloro-4-N-methylphenylamino-8-methoxyquinazoline (0.8 g, 0.0026 mol) and 4-fluoro-2-methylaniline (0.66 g, 0.0053 mol) were dissolved in ethanol (20 ml) placed in a pressure vessel and heated for 4 hours at 150°. After cooling the reaction mixture was evaporated to drynesss. The residue afforded crystals of 2-(2-methyl-4-fluorophenylamino)-4-(N-methylphenylamino)-8-methoxyquinazoline hydrochloride (0.25 g, 22%) from ethanolic hydrogen chloride, m.p. 218°-220°.

$C_{23}H_{21}N_4FO$ HCl

Found: C 64.87, H 5.19, N 13.05, Cl 8.16.
Requires: C 65.01, H 5.22, N 13.19, Cl 8.34.

EXAMPLE 42

Preparation of
2-(4-methoxy-2-methylphenyl)amino1-4-(N-methylphenylamino)quinazoline hydrochloride A. Preparation of
2-[(4-methoxy-2-methylphenyl)amino]quinazolin-4-one Substituting 4-methoxy-2-methylaniline (5.48 g) for o-toluidine and using corresponding molar proportions of other reagents in Example 33A gave 2-[(4-methoxy-2-methylphenyl)amino]quinazolin-4-one (4.35 g, 77%) crystallised from methanol, m.p. 270°-272°.

B. Preparation of
4-chloro-2-[(4-methoxy-2-methylphenyl)amino]-quinazoline

Substituting 2-[(4-methoxy-2-methylphenyl)amino]-quinazolin-4-one (3.6 g) for 2-(2-methylphenylamino)-quinazolin-4-one and using corresponding molar proportions of other reagents in Example 33B gave 4-chloro-2-[(4-methoxy-2-methylphenyl)amino]quinazoline (3.8 g) which was used without purification.

C. Preparation of
2-[(4-methoxy-2-methylphenyl)amino]-4-(N-methylphenylamino)quinazoline hydrochloride Substituting 4-chloro-2-[(4-methoxy-2-methylphenyl)amino]quinazoline (38 g) for 4-chloro-2-[(2-methylphenyl)amino]quinazoline and N-methylaniline for aniline in Example 33C gave the title compound (2.0 g, 38% - 2 steps) which was recrystallised from ethanol/diethyl ether as yellow needles, m.p. 248°-250°.

$C_{23}H_{22}N_4O.HCl.0.25 H_2O$

Found: C 67.01, H 5.72, N 13.52, Cl 8.33.
Requires: C 67.14, H 5.76, N 13.62, Cl 8.62.

EXAMPLE 43

Preparation of
4-(N-methylphenylamino)-2-(2-methylphenylamino)-6-methoxyquinazoline hydrochloride A. 2,4-Dihydroxy-6-methoxyquinazoline A mixture of 5-methoxy anthranilic acid (40 g, 0.24M), acetic acid (18.0 g, 0.3M) and 1 liter warm water (35°) was stirred and allowed to cool. A solution of potassium cyanate (24.3 g, 0.3M) in water (100 ml) was added over 15 minutes and then stirred for a further 30 minutes. Sodium hydroxide (320 g, 8.0M) solid was added portionwise and the reaction was then heated at 90° for 30 minutes and allowed to cool overnight. The solid was filtered off and dissolved in hot water (500 ml) and then acidified with dilute sulphuric acid to precipitate the product. The solid was filtered off and washed free of acid with water and then dried at 100°/vacuum to yield the title compound (37.7 g) m.p. >290°.

B. 2,4-Dichloro-6-methoxyquinazoline 2,4-Dihydroxy-6-methoxyquinazoline (37 g, 0.19M), phosphoryl chloride (95 ml) and dimethylaniline (40 ml) were heated under reflux for 3 hours. After cooling the reaction mixture was poured onto ice and the precipitated solid was filtered off, washed with water and air dried. The product was used immediately in the next stage.

C.
2-Chloro-4-(N-methylphenylamino)-6-methoxyquinazoline

A mixture of 2,4-dichloro-6-methoxyquinazoline, (38.3 g, 0.19M assuming 100% yield from previous step), N-methylaniline (19.26 g, 0.18M), sodium acetate (16.4 g, 0.2M) in tetrahydrofuran (2 liters) and water (1 liter) was stirred at room temperature for 8 days. Reaction was then concentrated to low volume (about 500 ml) and an oil separated out which solidified. The solid was filtered off and extracted with dichloromethane. Silica gel column chromatography followed by evaporation to dryness gave a residue which was washed with 40-60° petroleum ether (to remove trace impurity) to yield title compound (31.25 g) m.p. 133°-134°.

D. Preparation of
4-(N-methylphenylamino)-2-(2-methylphenylamino)-6-methoxyquinazoline hydrochloride A mixture of 2-chloro-4-(N-methylphenylamino)-6methoxyquinazoline (5.4 g, 0.027M), o-toluidine (4.28 g, 0.04M) in ethanol (50 ml) was heated in a Berchof pressure vessel at 140° for 5 hours (maximum pressure 40 psi). After cooling, ethanol/HCl was added and the solid which crystallised out was filtered off and recrystallised from isopropanol/ether to yield the title compound (4.23 g, m.p. 258°-260°).

EXAMPLE 44

4-(N-Methylphenylamino)-2-(2-methyl-4-fluorophenylamino)-6-methoxyquinazoline

2-Chloro-4-(N-methylphenylamino)-6-methoxyquinazoline (5.4 g, 0.02M) and 4-fluoro-2-methylaniline (4.96 g, 0.04M) were dissolved in ethanol (50 ml) and heated at 140° for 5 hours in a Berghof pressure reactor. The mixture was cooled and ethereal/HCl added. The precipitated solid was filtered off and recrystallised (isopropanol/ether followed by isopropanol) to yield the title compound (3.8 g) m.p. 248°–250°.

EXAMPLE 45

Preparation of 2-(2-methylphenylamino)-4-(N-methyl-4-methoxyphenylamino)quinazoline hydrochloride Substituting N-methyl-p-anisidine (3.18 g, 0.023 mol) for methylamine and using corresponding molar proportions of the other reagents in Example 34, gave after crystallisation 2-(2-methylphenylamino)-4-(N-methyl-4methoxyphenylamino)quinazoline hydrochloride (2.45 g, 33%), from ethanolic hydrogen chloride, m.p. 224°–226°.

EXAMPLE 46

Preparation of 2-(2-methylphenylamino)-4-(N-methyl-4-hydroxyphenylamino)quinazoline hydrochloride 2-(2-Methylphenylamino)-4-(N-methyl-4-methoxyphenylamino)quinazoline hydrochloride (1.6 g, 0.0043 mol) was stirred in dry dichloromethane (50 ml) at 0°–5° under nitrogen. To this solution was added boron tribromide (2.0 ml, 0.0216 mol) dropwise at 0°–5° over 10 minutes. The mixture was stirred for 3 hours at 0°–5° and then allowed to reach room temperature over 16 hours. After pouring onto ice, basifying and neutralising the aqueous phase was extracted with dichloromethane, the organic extracts which dried and evaporated to dryness. The residue afforded crystals of 2-(2-methylphenylamino)-4-(n-methyl-4-hydroxyphenylamino)quinazoline hydrochloride (0.4 g, 23.7%) from ethanolic hydrogen chloride m.p. 317°–319°.

EXAMPLE 47

Preparation of 2-[(4-chloro-2-methylphenyl)amino]-4-(N-methylphenylamino)quinazoline hydrochloride.

A. Preparation of 2-[(4-chloro-2-methylphenyl)amino]-4-(N-methylphenylamino)quinazolone.

Substituting 2-methyl-4-chloroaniline (2.6 g) for o-toluidine and using corresponding molar proportions of the other reagents in Example 33A gave the title compound (2.73 g), m.p. >270° (dec).

B. Preparation of 4-chloro-2-[(4-chloro-2-methylphenyl)amino]quinazoline.

Substituting 2-[(4-chloro-2-methylphenyl)amino]-4-quinazolone (2.5 g) for 2-[(2-methylphenyl)amino]-4-quinazolone and using corresponding molar proportions of the other reagents in Example 33B gave the title compound (1.0 g) which was used without purification.

C. Preparation of 2-[(4-chloro-2-methylphenyl)amino]-4-(N-methylphenylamino)quinazoline hydrochloride Substituting 4-chloro-2-[(4-chloro-2-methylphenyl)amino]quinazoline (1.0 g) and N-methylaniline (1.0 g) for the reagents in Example 33C and using analogous conditions and work-up gave the title compound (0.17 g), m.p. 263°–265°, after two recrystallisations from ethanol/diethyl ether.

EXAMPLE 48

Preparation of 2-(2-methylphenylamino)-4-(N-methylphenylamino)-8-fluoroquinazoline hydrochloride In a procedure analogous to that of Example 41 2-chloro-4-(N-methylphenylamino)-8-fluoroquinazoline and o-toluidine are reacted together to give the title compound. The starting 2-chloro-4-(N-methylphenylamino)8-fluoroquinazoline is prepared via procedures analogous to those of Example 1.

EXAMPLE 49

Preparation of 2-(2-methyl-4-fluorophenylamino)-4-(N-methylphenylamino)-8-fluoroquinazoline In a procedure analogous to that of Example 41 2-chloro-4-(N-methylphenylamino)-8-fluoroquinazoline and 2-methyl-4-fluoroaniline are reacted together to give the title compound.

EXAMPLE 50

Preparation of 2-(2-methylphenylamino)-4-(N-ethylphenylamino)quinazoline hydrochloride A. Preparation of 4-(N-ethylphenylamino)-2-chloroquinazoline.

Substituting N-ethylaniline for N-methylphenylamine and using corresponding molar proportions of other reagents in Example 26A, gives the title compound.

B. Preparation of 2-(2-methylphenylamino)-4-(N-ethylphenylamino)quinazoline hydrochloride.

Substituting 4-(N-ethylphenylamino)-2-chloroquinazoline for 4-(N-methylphenylamino)-2-chloroquinazoline and using molar proportions of the other reagents in Example 26B gives the title compound.

EXAMPLE 51

4-(N-Methylphenylamino)-2-(2-methylphenylamino)-8-hydroxyquinazoline 4-(N-Methylphenylamino)-2-(2-methylphenylamino)-8-methoxyquinazoline (prepared as described in co-pending EP-A-88311461.3) (1.81 g, 0.0049 mol) was dissolved in dichloromethane (50 ml) and cooled to 0°–5° under nitrogen. Boron tribromide (6.25 g, 0.025 mol) was added dropwise via a syringe through a rubber septum over a period of 10 minutes Reaction was stirred 3 hours at 0°–5° and then allowed to rise to room temperature overnight. The reaction mixture was poured onto ice and the pH adjusted to ~12 with sodium hydroxide and then back to neutral with dilute HCl. The organic layer was separated, dried and evaporated to dryness. The solid residue was crystallised from methanol/water to give the title compound (0.66 g), m.p. 174°–175°.

$C_{22}H_{20}N_4O$. 0.4 $H_2O$

Found: C 72.69, H 5.71, N 15.38.
Requires: C 72.67, H 5.77, N 15.41.

EXAMPLE 52

Bis-2,4-(N-methylphenylamino)-8-hydroxyquinazoline hydrochloride

Bis-2,4-(N-methylphenylamino)-8-methoxyquinazoline (prepared as described in co-pending EP-A-88311461.3) (4.5 g, 0.013 mol) was suspended in dichloromethane (100 ml) and cooled to 0°-5° in an atmosphere of nitrogen. Boron tribromide (16.5 g, 0.066 mol) was added dropwise from a syringe through a rubber septum. The reaction was stirred for three hours at 0°-5°, allowed to rise to room temperature overnight and poured onto ice. The aqueous phase was basified with sodium hydroxide and then neutralised with dilute HCl. The organic layer was separated, washed with water, dried and evaporated to dryness. The residue was chromatrographed on silica gel in ether. The product in ether was acidified with ethanolic hydrogen chloride (ethanol saturated with HCl gas) and the solid produced collected and recrystallised from isopropanol/ether to give the title compound (0.52 g) as its hydrochloride salt, m.p. 208°-210°.

$C_{22}H_{20}N_4O \cdot HCl \cdot 0.5 H_2O$

Found: C 65.97, H 5.37, N 13.62.
Requires: C 65.75, H 5.52, N 13.94.

EXAMPLE 53

4-(N-Methylphenylamino)-2-(2-methyl-4-fluorophenyl)amino]-8-hydroxyquinazoline hydrobromide 4-(N-Methylphenylamino)-2-[(2-methyl-4-fluorophenyl)amino]-8-methoxyquinazoline (prepared as described in co-pending EP-A-88311461.3) (6.75 g, 0.016 mol) was suspended in dichloromethane (150 ml) and the mixture cooled to 0°-5° under nitrogen. Boron tribromide (20 g, 0.08 mol) was added dropwise over 10 minutes with a syringe, keeping the temperature at 0°-5°. The mixture was stirred at room temperature overnight. Reaction was incomplete (t.l.c) so the mixture was heated at reflux temperature for eight hours, cooled and poured onto ice. The mixture was basified (NaOH) and then neutralised (dilute HCl), when an insoluble solid precipitated which was collected, washed with water, dried and crystallised from methanol to yield the title compound (2.8 g) as its hydrobromide salt, m.p. >300°.

$C_{22}H_{19}FN_4O \cdot HBr$

Found: C 58.02, H 4.39, N 12.12.
Requires: C 58.03, H 4.43, N 12.31.

EXAMPLE 54

8-(3-Dimethylaminopropoxy)-2-[(2-methylphenyl)amino]-4-(N-methylphenylamino)quinazoline Sodium metal (103 mg, 4.49 mM) was dissolved in absolute ethanol (20 ml) and the solution added to a suspension of 2-[(2-methylphenyl)amino]-4-(N-methylphenylamino)-8-hydroxyquinazoline (1.6 g, 4.49 mM) in ethanol (100 ml). The mixture was heated until a clear solution was produced and then the ethanol was evaporated off. Toluene (25 ml) was added and again the mixture was evaporated to dryness. The residue was dissolved in toluene (50 ml) and to this solution was added a solution of N,N-dimethylaminopropylchloride (546 mg, 4.49 mM) in toluene (75 ml). The resulting mixture was heated at reflux temperature overnight, cooled, washed with water (×2), dried and evaporated to dryness, to give a browny-yellow oil. This oil was crystallised from ether/pentane to give the title compound (0.9 g) as buff-coloured flakes, m.p. 77°-79°.

$C_{27}H_{31}N_5O$

Found: C 73.27, H 7.17, N 15.64.
Requires: C 73.44, H 7.08, N 15.86.

EXAMPLE 55

4-(N-Methylphenylamino)-2-[(2-methylphenyl)amino]-6-hydroxyquinazoline hydrobromide 4-(N-Methylphenylamino)-2-[(2-methylphenyl)amino]6-methoxyquinazoline (prepared as described in co-pending EP-A-88311461.3) (3.0 g, 0.0074 mol) and boron tribromide (9.2 g, 0.037 mol) were reacted together under the conditions described in Example 3 to give the title compound (1.39 g), crystallised from methanol/diethyl ether as its hydrobromide salt, m.p. 172°-174°.

$C_{22}H_{20}N_4O \cdot HBr \cdot 0.8 H_2O$

Found: C 58.61, H 5.04, N 12.39.
Requires: C 58.49, H 5.04, N 12.40.

EXAMPLE 56

4-(N-methylphenylamino)-2-[(2-methyl-4-fluorophenyl)amino]-6-hydroxyquinazoline hydrochloride 4-(N-methylphenylamino)-2-[(2-methyl-4-fluorophenyl)amino]-6-methoxyquinazoline (prepared as described in co-pending EP-A-88311461.3) (3.0 g, 0.007 mol) and boron tribromide (8.75 g, 0.035 mol) were reacted together and the product worked-up as described in Example 2. This gave the title compound as its hydrochloride salt (0.26 g) crystallised from isopropanol/ether, m.p. 258°-260°.

$C_{22}H_{19}FN_4O \cdot HCl$ (+2.5% I.P.A.)

Found: C 63.03, H 5.05, N 12.80.
Requires: C 62.92, H 5.09, N 12.81.

EXAMPLE 57

4-(N-methylphenylamino)-2-[(2-methyl-4-fluorophenyl)amino]-6-(3-dimethylaminopropoxy)quinazoline To a suspension of 4-(N-methylphenylamino)-2-[(2-methyl-4-fluorophenylamino]-6-hydroxyquinazoline hydrochloride (2.05 g, 0.005 mol) in ethanol (20 ml) was added a solution of sodium (0.23 g, 0.01 mol) in ethanol (15 ml). The resulting solution was evaporated to dryness, and the residue dissolved in dry toluene (25 ml) and brought to reflux temperature. To this solution was added a freshly prepared solution of N,N-dimethylaminopropylchloride in toluene (25 ml) (from 1.58 g, 0.01 mol of the hydrochloride) over 15 minutes under nitrogen. The reaction was heated at reflux temperature overnight, cooled, washed with aqueous $Na_2CO_3$ and water, dried and evaporated to dryness to give an oily residue. This was purified by column chromatography on silica gel using first ethyl acetate and then ethyl acetate/methanol, 5:1 as eluent. Fractions containing required product (pure by t.l.c) were combined, evaporated to dryness to give an oil which solidified under petroleum ether to give the title compound (0.6 g), m.p. 103°–104°.

$C_{27}H_{30}FN_5O$ (+1% $H_2O$)

Found: C 69.85, H 6.37, N 14.93.
Requires: C 69.85, H 6.62, N 15.08.

EXAMPLE 58

4-(N-methylphenylamino)-2-[(2-methyl-4-fluorophenyl)-amino]-6-(3-morpholinopropoxy)quinazoline Substituting 3-morpholinopropylchloride (from 2.0 g, 0.01 mol of hydrochloride) for N,N-dimethylaminopropyl chloride and using corresponding molar proportions of the other reagents in Example 7 gave, after removal of the toluene, an oily solid. This was crystallised from diethyl ether/pentane to give the title compound (1.34 g), m.p. 119°–120°.

$C_{29}H_{32}FN_5O_2$

Found: C 69.71, H 6.40, N 13.66.
Requires: C 69.44, H 6.43, N 13.96.

EXAMPLE 59

4-(N-methylphenylamino)-2-[(2-methyl-4-fluorophenyl)amino]-6-(2-dimethylaminoethoxy)quinazoline Substituting N,N-dimethylaminoethylchloride (from 1.44 g, 0.01 mole of hydrochloride) from N,N-dimethylaminopropylchloride and using corresponding molar proportions of the other reagents in Example 7 gave, after cooling, the reaction mixture in toluene. This was worked with water, followed by 2N HCl. The HCl washings were basified with 2N.NaOH and extracted with dichloromethane. The dichloromethane was washed with water, dried and evaporated to dryness. The residue was purified by column chromatography on silica gel using ethyl acetate/methanol, 10:1 as eluent. Combination of the appropriate fractions (t.l.c) and evaporation gave an oily residue. This was crystallised from diethyl ether/pentane to yield the title compound (0.73 g), m.p. 112°–114°.

EXAMPLE 60

8-(Hydroxyethoxy)-4-(N-methylphenylamino)-2-[(2-methylphenyl)amino]quinazoline (i) Sodium hydride (0.325 g of 50% dispersion in oil 6.75 mmol) was added to dry DMF (30 ml) and to the stirred solution under dry nitrogen was added a solution of 8-hydroxy-2-[(2-methylphenyl)amino]-4-(N-methylphenylamino)quinazoline (2.4 g, 6.75 mmol) in dry DMF (30 ml). After stirring at room temperature for one hour (solution goes from greeny-yellow to red-brown) a solution of ethyl bromoacetate (1.125 g, 6.75 mmol) in dry DMF (30 ml) was added dropwise over 0.5 hour. The resulting mixture was stirred at room temperature for four hours, water added followed by aq. $Na_2CO_3$. The mixture was extracted with ethyl acetate (×2) and the organic extracts combined, washed with water, dried and evaporated to give a green oil (2.9 g).

This material was chromatographed on silica gel using $CH_2Cl_2$ as initial eluent. Fractions were monitored by thin-layer chromatography and the major product was eluted with $CH_2Cl_2$/1% methanol. Relevant fractions were combined and evaporated to dryness to give 8-(ethoxycarbonylmethoxy)-4-(N-methylphenylamino)-2-[(2-methylphenyl)amino]quinazoline as a green glass (2.4 g).

(ii) Lithium aluminium hydride (0.27 g, 7.1 mmol) was added to dry distilled THF (50 ml) and the mixture stirred in an ice-bath under dry nitrogen. A solution of 8-(ethoxycarbonylmethoxy)-4-(N-methylphenylamino)-2-[(2-methylphenyl)amino]quinazoline (2.4 g, 5.43 mmol) in dry THF (30 ml) was added dropwise at such a rate as to keep the reaction temperature below 5°. The mixture was then allowed to freely reach room temperature and stirred for three hours. Water was carefully added followed by a little 40% NaOH. Two layers were produced and this mixture was extracted (×2) with ethyl acetate. The combined organic extracts were worked with water (×3) and brine, dried ($Na_2SO_4$) and evaporated to give an oil which crystallised on scratching to a yellow solid (1.9 g).

This material was crystallised twice from acetone/diethyl ether to give the title compound (0.66 g) as a yellow solid, m.p. 158°–160°.

$C_{24}H_{24}N_4O_2$

Found: C 71.87, H 6.22, N 13.60.
Requires: C 71.98, H 6.04, N 13.99.

EXAMPLE 61

2-(2-Methyl-4-fluorophenylamino)-4-(N-methylphenylamino)-8-(3-morpholinopropoxy)quinazoline 2-(2-Methyl-4-fluorophenylamino)-4-(N-methylphenylamino)-8-hydroxyquinazoline (1.6 g, 4.3 mmol) was suspended in ethanol (25 ml) and to the stirred suspension was added a solution of sodium (0.1 g, 4.3 mmol) in ethanol (15 ml). Stirring was continued for 15 minutes and the mixture evaporated to dryness. The residue was dissolved in toluene (50 ml) and heated to reflux temperature. To this refluxing solution was added a freshly prepared solution of 3-morpholinopropyl chloride base (from 1.28 g, 6.4 mmol of hydrychloride salt) in toluene (20 ml). Refluxing was continued overnight and after cooling the mixture was washed with sodium carbonate solution and water, dried and evaporared. The residual oil was chromatographed on silica gel using $CH_2Cl_2$ as eluting solvent. After evaporation of the relevent fractions the residue was crystallised from diethyl ether/pentane to give the title compound (1.5 g, 71%) m.p. 133°–134°.

$C_{29}H_{32}F N_5O_2$

Found: C 69.23, H 6.54, N 13.82.
Requires: c 69.44, B 6.43, N 13.96.

EXAMPLE 62

2-(2-Methyl-4-fluorophenylamino)-4-(N-methylphenylamino)-8-(3-dimethylaminopropoxy)quinazoline Substituting N,N-dimethylaminpropyl chloride hydrochloride (1.6 g, 8.6 mmol) for 3-morpholinopropyl chloride hydrochloride in Example 11 and using corresponding molar proportions of the other reagents gave an oily solid after chromatography. This was crystallised from diethylether/pentane to give the title compound (1.04 g, 53%), m.p. 110°–112°.

$C_{27} H_{30}F N_5O$

Found: C 70.51, H 6.55, N 15.01.

Requires: C 70.56, H 6.58, N 15.24.

Biological Data

(A) H+K+ATPase Activity

The effects of a single high concentration (100 μM) of a compound of structure (I) on K-stimulated ATPase activity in lyophilised gastric vesicles was determined. Preferred compounds of structure (I) were also tested over a range of concentrations to determine $IC_{50}$ values.

(i) Preparation of lyophilised gastric vesicles (H/K-ATPase)

Lyophilised gastric vesicles were prepared from pig fundic mucosa after the method of Keeling et. al. (Biochem. Pharmacol., 34, 2967, 1985).

(ii) K+-stimulated ATPase activity

K+-stimulated ATPase activity was determined at 37° in the presence of the following: 10 mM Pipes/Tris buffer pH 7.0, 2 mM $MgSO_4$, 1 mM KCl, 2 mM $Na_2ATP$ and 3-6 μg protein/ml lyophilised gastric vesicles. After incubation for 30 minutes, the inorganic phosphate hydrolysed from ATP was determined by the method of Yoda and Hokin (Biochem. Biophys. Res. Commun. 40, 880, 1970).

Compounds of structure (I) were dissolved in dimethylsulphoxide which up to the highest concentration used had no effect on K+-stimulated ATPase activity.

The effect of the highest concentration of each compound of structure (I) on the recovery of a standard amount of inorganic phosphate was also determined.

(iii) Results.

The compounds of the examples had $IC_{50}$ values in the range of from 0.02 to 30 μM.

B. Rat: Lumen perfused stomach (pentagastrin stimulated gastric acid secretion)

Using a modification of the procedure described by Ghosh and Schild (Br. J. Pharmacology, 13, 54, 1958), the compounds of the following Examples were found on i.v. administration at a concentration of 10 μmole/kg to cause an inhibition of pentagastrin stimulated gastric acid secretion as indicated in the following Table.

| Compound | Rat G.S. % inhibition @ 10 μmole/kg |
| --- | --- |
| 1 | 60 |
| 2 | 25 |
| 3 | 16 |
| 4 | 37 |
| 5 | 37 |
| 6 | 48 |
| 7 | 20 |
| 8 | 17 |
| 11 | 28 |
| 13 | 20 |
| 15 | 31 |
| 16 | 31 |
| 18 | 12 |
| 20 | 72 |
| 21 | 37 |
| 22 | 27 |
| 24 | 97 |
| 25 | 24 |
| 26 | 79 |
| 27 | 71 |
| 29 | 13 |
| 30 | 23 |
| 31 | 8 |

-continued

| Compound | Rat G.S. % inhibition @ 10 μmole/kg |
| --- | --- |
| 32 | 96 |

(C) Bone resorption inhibitory activity

Bone resorption was measured by the actions of isolated rat osteoclasts on cortical bone slices (Zaidi et al Quarterly Journal of Experimental Physiology 1988 73:471-485). Newborn Wistar rats were killed by decapitation and their femora and tibiae removed. Osteoclasts were mechanically disaggregated by curetting the bones into medium followed by agitation with a pipette. Osteoclasts were separated from other cells by sedimentation onto bone slices (15 minutes, 37°) after which the slices were removed and gently washed. The bone slices were then incubated in the presence of test compounds (37°, 10% humidified $CO_2$, 18 hours) and fixed with glutaraldehyde. The degree of bone resorption was then assessed by the area of erosions produced by the osteoclasts using scanning electron microscopy. Data were meaned from measurements of 6 bone slices in each of two independent experiments.

Test compounds were dissolved in ethanol which was also added to control incubations (1%) in the absence of compound.

| | Conc. (μM) | Bone resorption (%) |
| --- | --- | --- |
| Control | | 100 ± 27 |
| Example 56 | 10 | 7 ± 4 |
| | 100 | 7 ± 0 |

Mean ± SEM, n = 12

EXAMPLE A

A tablet for oral administration is prepared by combining

| | Mg/Tablet |
| --- | --- |
| Compound of structure (I) | 100 |
| lactose | 153 |
| Starch | 33 |
| crospovidone | 12 |
| microcrystalline cellulose | 30 |
| magnesium stearate | 2 |
| | 330 mg | into a 9 mm tablet.

EXAMPLE B

An injection for parenteral administration was prepared from the following

| | % w:w |
| --- | --- |
| Compound of Example 20 | 0.50% (w:v) |
| 1M citric acid | 30% (v:v) |
| sodium hydroxide (qs) | to pH 3.2 |
| water for injection EP | to 100 ml |

The compound of Example 20 was dissolved in the citric acid and the pH slowly adjusted to pH 3.2 with the sodium hydroxide solution. The solution was then made up to 100 ml with water, sterilised by filtration and sealed into appropriately sized ampoules and vials.

What we claim is:
1. A compound of structure (I)

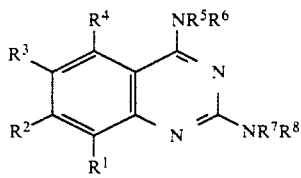

in which

R$^1$ to R$^4$ are the same or different and are each hydrogen, C$_{1-4}$alkyl, C$_{1-4}$alkoxy, phenyl, C$_{1-4}$alkylthio, C$_{1-4}$alkanoyl, amino, C$_{1-6}$alkylamino, diC$_{1-4}$alkylamino, halogen, trifluoromethyl, hydroxy, hydroxyC$_{1-4}$-alkyl, carboxyC$_{1-4}$alkoxy, hydroxyC$_{1-4}$alkoxy, C$_{1-4}$alkoxyC$_{1-4}$alkoxy, O(CH$_2$)$_m$Het, C$_{1-4}$alkylNR$^9$R$^{10}$ or O(CH$_2$)$_m$NR$^9$R$^{10}$ in which m is 2 to 4 and R$^9$ and R$^{10}$ are the same or different and are each hydrogen, C$_{1-4}$alkyl, Het or —(CH$_2$)$_n$Ar, or R$^9$ and R$^{10}$ together with the nitrogen to which they are attached form a piperidino, morpholino, imadazolyl, pyridyl or pyrrolidine ring; provided that at least two of R$^1$ to R$^4$ are hydrogen;

R$^5$ and R$^6$ are the same, or different and are each hydrogen, C$_{1-4}$alkyl, —(CH$_2$)$_n$Ar, or R$^5$ and R$^6$ together with the nitrogen atom to which they are attached form a piperidino, morpholino, imidazolyl, pyridyl or pyrrolidine ring;

R$^7$ and R$^8$ are the same or different and are each hydrogen, C$_{1-4}$alkyl, (CH$_2$)$_n$Ar$^1$, or R$^7$ and R$^8$ together with the nitrogen atom to which they are attached form a piperidino, morpholino, imidazolyl, pyridyl or pyrrolidine ring;

n is 0 to 4;
Ar is phenyl;
Ar$^1$ is phenyl;
Het is pyridyl or imidazolyl,

Wherein Ar, Ar$^1$ and Het may be unsubstituted or substituted by 1 to 3 substituents selected from C$_{1-4}$alkyl, C$_{1-4}$alkoxy, C$_{1-4}$alkylthio, halogen, cyano, amino, hydroxy, carbamoyl, carboxy, C$_{1-4}$alkanoyl or trifluoromethyl;

and pharmaceutically acceptable salts thereof, provided that:

when R$^1$ to R$^4$ are the same or different and are each hydrogen, C$_{1-4}$alkyl, C$_{1-4}$alkoxy, phenyl, C$_{1-4}$alkylthio, C$_{1-4}$alkanoyl, amino, C$_{1-4}$alkylamino, diC$_{1-4}$-alkylamino, halogen or trifluoromethyl, then (a) R$^5$, R$^6$, R$^7$ and R$^8$ are not all hydrogen;
(b) at least one of R$^5$ or R$^6$ is (CH$_2$)$_n$Ar; or R$^7$ or R$^8$ is (CH$_2$)$_n$Ar$^1$;
(c) when R$^1$ and R$^4$ are hydrogen, and either one of R$^2$ or R$^3$ is C$_{1-4}$alkoxy, the other is not hydrogen or C$_{1-4}$alkoxy.

2. A compound according to claim 1 in which R$^2$ to R$^4$ are hydrogen and R$^1$ is hydrogen, C$_{1-4}$alkoxy or hydroxy or O(CH$_2$)$_m$NR$^9$R$^{10}$ in which m, R$^9$ and R$^{10}$ are as described in claim 1.

3. A compound according to claim 2 in which one of R$^5$ and R$^6$ is (CH$_2$)$_n$Ar in which n is 0 to 4 and Ar is an optionally substituted phenyl group and the other is C$_{1-4}$alkyl.

4. A compound according to claim 3 in which n is 0.

5. A compound according to claim 4 in which one of R$^7$ and R$^8$ is hydrogen and the other is —(CH$_2$)$_n$Ar$^1$ in which n is 0 to 4 and Ar$^1$ is an optionally substituted phenyl group.

6. A compound according to claim 1 which is 2-amino-8-methoxy-4-(2-methylphenylamino)quinazoline.

7. A compound according to claim 1 which is 2,4-Bis-(N-methylphenylamino)quinazoline.

8. A compound according to claim 1 which is 4-(N-methylphenylamino)-2-(2-methylphenylamino)-8-methoxyquinazoline.

9. A compound according to claim 1 which is 2-(2-methylphenylamino)-4-(N-methylphenylamino)-quinazoline.

10. A compound according to claim 1 which is 2-phenylamino-4-(N-methylphenylamino)quinazoline.

11. A compound according to claim 1 which is 2-[(2-methyl-4-fluorophenyl)amino]-4-(N-methylphenylamino)quinazoline.

12. A compound according to claim 1 which is 2-(2-methylphenylamino)-4-phenylaminoquinazoline.

13. A compound according to claim 1 which is 4-(N-Methylphenylamino)-2-(2-methylphenylamino)-8-hydroxyquinazoline.

14. A compound according to claim 1 which is bis-2,4-(N-methylphenylamino)-8-hydroxyquinazoline hydrochloride.

15. A compound according to claim 1 which is 4-(N-methylphenylamino)-2-[(2-methyl-4-fluorophenyl)amino]-8-hydroxyquinazoline hydrobromide.

16. A compound according to claim 1 which is 8-(3-dimethylaminopropoxy)-2-[(2-methylphenyl)amino]-4-(N-methylphenylamino)quinazoline.

17. A compound according to claim 1 which is 4-(N-methylphenylamino)-2-[(2-methylphenyl)amino]-6-hydroxyquinazoline hydrobromide.

18. A compound according to claim 1 which is 4-(N-methylphenylamino)-2-[(2-methyl-4-fluorophenyl)amino]-6-hydroxyquinazoline hydrochloride.

19. A compound according to claim 1 which is 4-(N-methylphenylamino)-2-[(2-methyl-4-fluorophenyl)amino]-6-(3-dimethylaminopropoxy)quinazoline.

20. A compound according to claim 1 which is 4-(N-methylphenylamino)-2-[(2-methyl-4-fluorophenyl)amino]-6-(3-morpholinopropoxy)quinazoline.

21. A compound according to claim 1 which is 4-(N-methylphenylamino)-2-[(2-methyl-4-fluorophenyl)amino]-6-(2-dimethylaminoethoxy)quinazoline.

22. A pharmaceutical composition comprising a compound of structure (I) according to claim 1 and a pharmaceutical carrier.

23. A pharmaceutical composition according to claim 22 in which the compound of structure (I) is 2-amino-8-methoxy-4-(2-methylphenylamino)quinazoline.

24. A pharmaceutical composition according to claim 22 in which the compound of structure (I) is 2,4-Bis-(N-methylphenylamino)quinazoline.

25. A pharmaceutical composition according to claim 22 in which the compound of structure (I) is 4-(N-methylphenylamino)-2-(2-methylphenylamino)-8-methoxyquinazoline.

26. A pharmaceutical composition according to claim 22 in which the compound of structure (I) is 2-(2-methylphenylamino)-4-(N-methylphenylamino)-quinazoline.

27. A pharmaceutical composition according to claim 22 in which the compound of structure (I) is 2-phenylamino-4-(N-methylphenylamino)quinazoline.

28. A pharmaceutical composition according to claim 22 in which the compound of structure (I) is 2-[(2-methyl-4-fluorophenyl)amino]-4-(N-methylphenylamino)quinazoline.

29. A pharmaceutical composition according to claim 22 in which the compound of structure (I) is 2-(2-methylphenylamino)-4-phenylaminoquinazoline.

30. A compound according to claim 1 which is 4-(N-methylphenylamino)-2-(2-methylphenylamino)-8-hydroxyquinazoline.

31. A compound according to claim 1 which is bis-2,4-(N-methylphenylamino)-8-hydroxyquinazoline hydrochloride.

32. A compound according to claim 1 which is 4-(N-methylphenylamino)-2-[(2-methyl-4-fluorophenyl)amino]-8-hydroxyquinazoline hydrobromide.

33. A compound according to claim 1 which is 8-(3-dimethylaminopropoxy)-2-[(2-methylphenyl)amino]-4-(N-methylphenylamino)quinazoline.

34. A compound according to claim 1 which is 4-(N-methylphenylamino)-2-[(2-methylphenyl)amino]-6-hydroxyquinazoline hydrobromide.

35. A compound according to claim 1 which is 4-(N-methylphenylamino)-2-[(2-methyl-4-fluorophenyl)amino]-6-hydroxyquinazoline hydrochloride.

36. A compound according to claim 1 which is 4-(N-methylphenylamino)-2-[(2-methyl-4-fluorophenyl)amino]-6-(3-dimethylaminopropoxy)quinazoline.

37. A compound according to claim 1 which is 4-(N-methylphenylamino)-2-[(2-methyl-4-fluorophenyl)amino]-6-(3-morpholinopropoxy)quinazoline.

38. A compound according to claim 1 which is 4-(N-methylphenylamino)-2-[(2-methyl-4-fluorophenyl)amino]-6-(2-dimethylaminoethoxy)quinazoline or a pharmaceutically acceptable salt thereof.

39. A method of treating gastric acid secretion which comprises administering to a mammal in need thereof an effective amount of a compound of structure (IA)

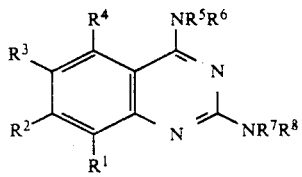

$R^1$ to $R^4$ are the same or different and are each hydrogen, $C_{1-4}$alkyl, $C_{1-4}$alkoxy, phenyl, $C_{1-4}$alkylthio, $C_{1-4}$alkanoyl, amino, $C_{1-6}$alkylamino, di$C_{1-4}$alkylamino, halogen, trifluoromethyl, hydroxy, hydroxy$C_{1-4}$-alkyl, carboxy$C_{1-4}$alkoxy, hydroxy$C_{1-4}$alkoxy, $C_{1-4}$alkoxy$C_{1-4}$alkoxy, $O(CH_2)_m$Het, $C_{1-4}$alkyl$NR^9R^{10}$ or $O(CH_2)_mNR^9R^{10}$ in which m is 2 to 4 and $R^9$ and $R^{10}$ are the same or different and are each hydrogen, $C_{1-4}$alkyl, Het or $-(CH_2)_n$Ar, or $R^9$ and $R^{10}$ together with the nitrogen to which they are attached form a piperidino, morpholino, imadazolyl, pyridyl or pyrrolidine ring; provided that at least two of $R^1$ to $R^4$ are hydrogen;

$R^5$ and $R^6$ are the same, or different and are each hydrogen, $C_{1-4}$alkyl, $-(CH_2)_n$Ar, or $R^5$ and $R^6$ together with the nitrogen atom to which they are attached form a piperidino, morpholino, imidazolyl, pyridyl or pyrrolidine ring;

$R^7$ and $R^8$ are the same or different and are each hydrogen, $C_{1-4}$alkyl, $(CH_2)_n Ar^1$, or $R^7$ and $R^8$ together with the nitrogen atom to which they are attached form a piperidino, morpholino, imidazolyl, pyridyl or pyrrolidine ring;

n is 0 to 4;

Ar is phenyl;

$Ar^1$ is phenyl;

Het is pyridyl or imidazolyl,

Ar, $Ar^1$ and Het may be unsubstituted or substituted by 1 to 3 substituents selected from $C_{1-4}$alkyl, $C_{1-4}$alkoxy, $C_{1-4}$alkylthio, halogen, cyano, amino, hydroxy, carbamoyl, carboxy, $C_{1-4}$alkanoyl or trifluoromethyl;

or a pharmaceutically acceptable salt thereof.

40. A method of treatment of diseases of the stomach or intestine based on increased acid secretion which comprises administering to a mammal in need thereof an effective amount of a compound of structure (IA) as described in claim 39.